US008591915B2

(12) United States Patent
Buetow et al.

(10) Patent No.: US 8,591,915 B2
(45) Date of Patent: Nov. 26, 2013

(54) PLANT-DERIVED VACCINES AGAINST RESPIRATORY SYNCYTIAL VIRUS

(76) Inventors: Dennis E. Buetow, Champaign, IL (US); Schuyler S. Korban, Champaign, IL (US); Jagdeep Sandhu, Urbana, IL (US); Sergei F. Krasnyanski, Raleigh, NC (US)

( * ) Notice: Subject to any disclaimer, the term of this patent is extended or adjusted under 35 U.S.C. 154(b) by 0 days.

(21) Appl. No.: 13/194,194

(22) Filed: Jul. 29, 2011

(65) Prior Publication Data
US 2011/0300180 A1    Dec. 8, 2011

Related U.S. Application Data

(63) Continuation of application No. 12/847,401, filed on Jul. 30, 2010, now abandoned, which is a continuation of application No. 10/947,211, filed on Sep. 23, 2004, now abandoned, which is a continuation of application No. 09/568,018, filed on May 10, 2000, now abandoned.

(60) Provisional application No. 60/133,536, filed on May 11, 1999.

(51) Int. Cl.
*A61K 39/155*    (2006.01)
(52) U.S. Cl.
USPC ........................................................ 424/211.1
(58) Field of Classification Search
None
See application file for complete search history.

(56) References Cited

U.S. PATENT DOCUMENTS

| 4,956,282 | A | | 9/1990 | Goodman et al. | ......... 435/69.51 |
| 5,530,191 | A | | 6/1996 | Maliga | |
| 5,612,487 | A | * | 3/1997 | Lam et al. | ..................... 800/288 |
| 5,914,123 | A | | 6/1999 | Arntzen et al. | |

FOREIGN PATENT DOCUMENTS

| FR | 2748480 | 11/1997 |
| WO | WO92/07940 | 5/1992 |
| WO | WO94/20135 | 9/1994 |
| WO | WO97/10347 | 3/1997 |

OTHER PUBLICATIONS

Collins et al. (Fields Virology, 3rd Edition) pp. 139-140 year 1996.*
Srikiatkhachorn et al., J of Experimental Medicine 1997, 186: 421-432.*
A vaccine for RSV: Is it possible—By Debra A. Tristram, MD, and Robert C. Welliver, MD.
Adjuvants influence the quantitative and qualitative immune response in BALB/c mice immunized with respiratory syncytial virus FG subunit vaccine.
Recombinant Human Respiratory Syncytial IBirus (RSV) from cDNA and Construction of Subgroup A and B Chimeric RSV.
Enhanced pulmonary pathology associated with the use of formalin-inactivated respiratory syncytial virus vaccine in cotton rats is not a unique viral phenomenon*.
Purified fusion protein vaccine protects against lower respiratory tract illness during respiratory syncytial virus season in children with cystic fibrosis.
Transgenic plants as vaccine production system—Hugh S. Mason and Charles J. Arntzen.
Therapeutic concepts A public of the Pharmacy Department vol. XIV.
Respiratory Syncytial Birus—Kenneth McIntosh and Robert M. Chanock.
Enhanced expression of the human respiratory syncytial virus-F gene in apple leaf protoplasts.
Sandhu, J. et al., *Enhanced Expression of the Human Respiratory Syncytial Virus-F Gene in Apple Leaf Protoplasts*, Plant Cell Reports, (1999), pp. 394-397.
Mason, H., et al., *Expression of Norwalk Virus Capsid Protein in Transgenic Tobacco and Potato and Its Oral Immunogenicity in Mice*, Proc. Natl. Acad. Sci., USA, May 1996, pp. 5335-5340.
Wigforovitz, A., et al., *Induction of a Protective Antibody Response to Foot and Mouth Disease Virus in Mice Following Oral or Parenteral Immunization with Alfalfa Transgenic Plants Expressing the Viral Structural Protein VP$^1$*, Virology, Mar. 15, 1999, pp. 347-353.
Sandhu, J., et al., *Oral Immunization of Mice with Transgenic Tomato Fruit Expressing Respiratory Syncytial Virus-F Protein Induces a Systemic Immune Response*, Transgenic Research, (2000), 9(2), pp. 127-135.
Kozie et al., Biotechnology 1993, 11 (FEB) 194-200.
Fields Virology, 3rd Edition, pp. 139-1340.
Collins et al., Proc Natl Acad Sci USA Dec. 1984; 81(24):7683-7.
Wertz et al., Proc Natl Acad Sci USA Jun. 1985; 82(12):4075-4079.
Murray et al., Nucleic Acid Research 1989, 17 (2) pp. 477-498.
The Illustrated Dictionary of Immunology Eds Cruse and Lewis, CRC Press 1998.
Srikiatkhachom et al., J of Experimental Medicine 1997, 186: 421-432.
Sandhu et al., Plant Mol Bio, 1998, pp. 885-896.

(Continued)

*Primary Examiner* — Mary E. Mosher
*Assistant Examiner* — Myron Hill
(74) *Attorney, Agent, or Firm* — Licata & Tyrrell, P.C.

(57) ABSTRACT

A plant-derived vaccine against respiratory syncytial virus (RSV) is disclosed. The vaccine includes an immunogenic complex that includes plant cells transformed with a chimeric gene containing a nucleotide sequence adapted for protein expression in plants and an RSV coding sequence that encodes an antigenic protein of RSV. Also disclosed are methods of making the plant-derived vaccine of the invention, as well as transgenic plants, transgenic plant cells, and nucleic acid constructs useful in immunizing a mammal against RSV.

3 Claims, 13 Drawing Sheets

(56) References Cited

OTHER PUBLICATIONS

Fields, Bernard, N., et al. Fields Virology, "Respiratory Syncytial Virus." 3rd Edition, vol. 1, pp. 1339-1340.
Collins, Peter, L., et al., "Nucleotide sequence of the gene encoding the fusion (F) glycoprotein of human respiratory syncytial virus." Proc Natl Acad Sci USA Dec. 1984; 81(24):7683-7687.
Wertz, Gail, W., et al., "Nucleotide sequence of the G protein gene of human respiratory syncytial virus reveals an unusual type of viral membrane protein." Proc Natl Acad Sci USA Jun. 1985; vol. 82(12):4075-4079.
Murray, Elizabeth E., et al., "Codon Usage in plant genes." Nucleic Acid Research 1989, 17 (2) pp. 477-498.
Srikiatkhachorn, Anon., et al. "Virus-specific CD8$^+$T Lymphocytes Downregulate T Helper Cell Type 2 Cytokine Secretion and Pulmonary Eosinophilia during Experimental Murine Respiratory Syncytial Virus Infection." J of Experimental Medicine 1997, 186: 421-432.
Chen et al., "Regulatory T Cell Clones Induced by oral Tolerance: Suppression of Autoimmune Encephalomyelitis", Science 1994 265:1237-1240.
Kahn, Jeffrey S., "Respiratory syncytial virus vaccine development", Current Opinion in Pediatrics 2000 12:257-262.
Tacket et al., "Immunogenicity in humans of a recombinant bacterial antigen delivered in a transgenic potato", Nat. Med. 1998 4(5):607-609.
Murphy et al. An update on approaches to the development of respiratory syncytial virus (RSV) and parainfluenza virus type 3 (PIV3) vaccines. Virus Research 1994 vol. 32, pp. 13-36.
Mason et al., Transgenic plants as vaccine production systems, Trends in Biotechnology, vol. 13, Issue 9, , Sep. 1995, pp. 388-392.
Collins et al. in Fields Virology 3$^{rd}$ Ed. pp. 1339-1340.

* cited by examiner

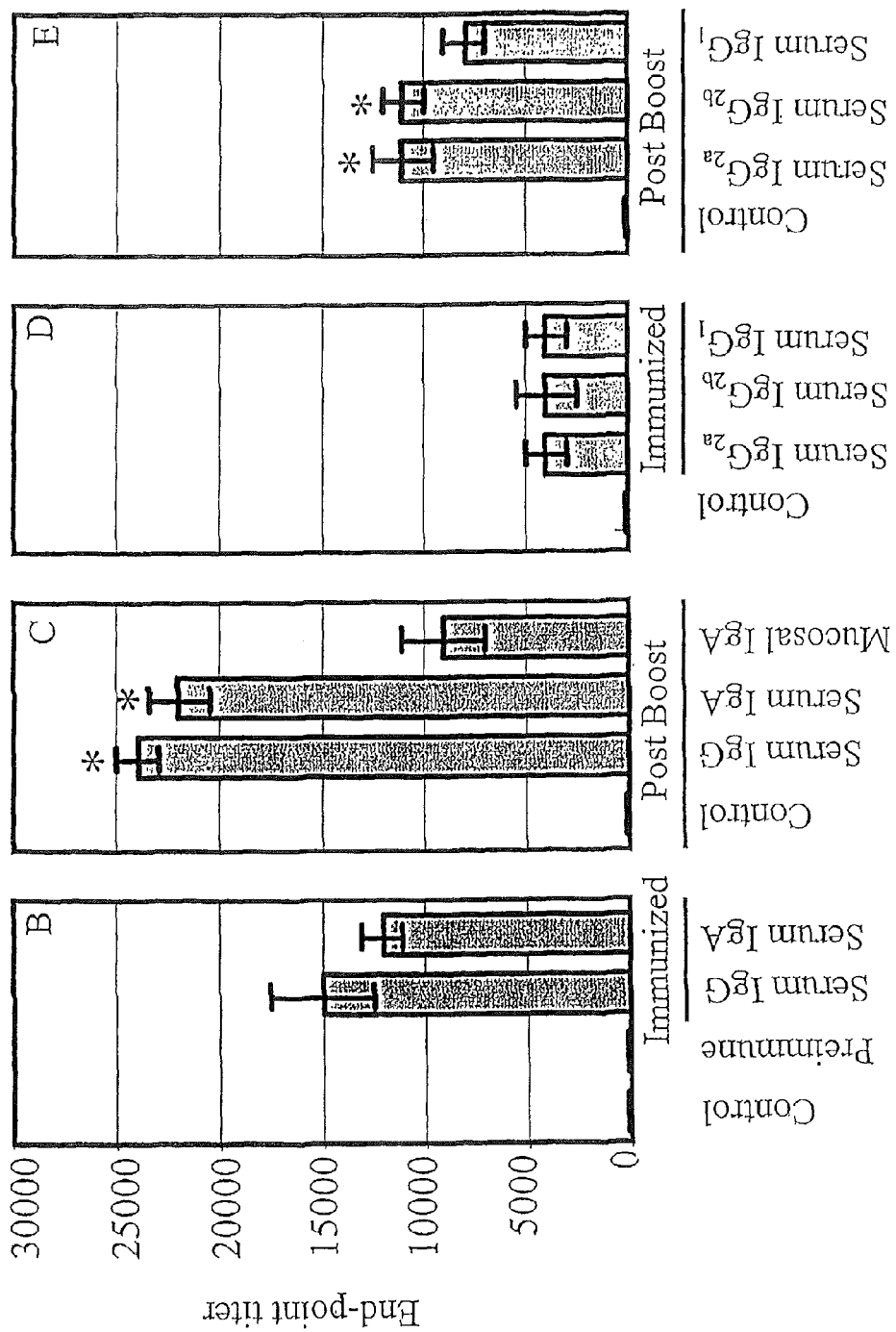

Human RSV F-protein gene
LOCUS     7938     1899 bp
DEFINITION 7938     1899 bp, 1899 bases, 7650C88 checksum.
ORIGIN 1 GGGGCAAATA ACAATGGAGT TGCTAATCCT CAAAGCAAAT GCAATTACCA
51 CAATCCTCAC TGCAGTCACA TTTTGTTTTG CTTCTGGTCA AAACATCACT
101 GAAGAATTTT ATCAATCAAC ATGCAGTGCA GTTAGCAAAG GCTATCTTAG
151 TGCTCTGAGA ACTGGTTGGT ATACCAGTGT TATAACTATA GAATTAAGTA
201 ATATCAAGGA AAATAAGTGT AATGGAACAG ATGCTAAGGT AAAATTGATA
251 AAACAAGAAT TAGATAAATA TAAAAATGCT GTAACAGAAT TGCAGTTGCT
301 CATGCAAAGC ACACCACCAA CAAACAATCG AGCCAGAAGA GAACTACCAA
351 GGTTTATGAA TTATACACTC AACAATGCCA AAAAAACCAA TGTAACATTA
401 AGCAAGAAAA GGAAAAGAAG ATTTCTTGGT TTTTTGTTAG GTGTTGGATC
451 TGCAATCGCC AGTGGCGTTG CTGTATCTAA GGTCCTGCAC CTAGAAGGGG
501 AAGTGAACAA GATCAAAAGT GCTCTACTAT CCACAAACAA GGCTGTAGTC
551 AGCTTATCAA ATGGAGTTAG TGTCTTAACC AGCAAAGTGT TAGACCTCAA
601 AAACTATATA GATAAACAAT TGTTACCTAT TGTGAACAAG CAAAGCTGCA
651 GCATATCAAA TATAGAAACT GTGATAGAGT TCCAACAAAA GAACAACAGA
701 CTACTAGAGA TTACCAGGGA ATTTAGTGTT AATGCAGGTG TAACTACACC
751 TGTAAGCACT TACATGTTAA CTAATAGTGA ATTATTGTCA TTAATCAATG
801 ATATGCCTAT AACAAATGAT CAGAAAAAGT TAATGTCCAA CAATGTTCAA
851 ATAGTTAGAC AGCAAAGTTA CTCTATCATG TCCATAATAA AAGAGGAAGT
901 CTTAGCATAT GTAGTACAAT TACCACTATA TGGTGTTATA GATACACCCT
951 GTTGGAAACT ACACACATCC CCTCTATGTA CAACCAACAC AAAAGAAGGG
1001 TCCAACATCT GTTTAACAAG AACTGACAGA GGATGGTACT GTGACAATGC
1051 AGGATCAGTA TCTTTCTTCC CACAAGCTGA AACATGTAAA GTTCAATCAA
1101 ATCGAGTATT TTGTGACACA ATGAACAGTT TAACATTACC AAGTGAAATA
1151 AATCTCTGCA ATGTTGACAT ATTCAACCCC AAATATGATT GTAAAATTAT
1201 GACTTCAAAA ACAGATGTAA GCAGCTCCGT TATCACATCT CTAGGAGCCA
1251 TTGTGTCATG CTATGGCAAA ACTAAATGTA CAGCATCCAA TAAAAATCGT
1301 GGAATCATAA AGACATTTTC TAACGGGTGC GATTATGTAT CAAATAAAGG
1351 GATGGACACT GTGTCTGTAG GTAACACATT ATATTATGTA AATAAGCAAG
1401 AAGGTAAAAG TCTCTATGTA AAAGGTGAAC CAATAATAAA TTTCTATGAC
1451 CCATTAGTAT TCCCCTCTGA TGAATTTGAT GCATCAATAT CTCAAGTCAA
1501 CGAGAAGATT AACCAGAGCC TAGCATTTAT TCGTAAATCC GATGAATTAT
1551 TACATAATGT AAATGCTGGT AAATCCACCA CAAATATCAT GATAACTACT
1601 ATAATTATAG TGATTATAGT AATATTGTTA TCATTAATTG CTGTTGGACT
1651 GCTCTTATAC TGTAAGGCCA GAAGCACACC AGTCACACTA AGCAAAGATC
1701 AACTGAGTGG TATAAATAAT ATTGCATTTA GTAACTAAAT AAAAATAGCA
1751 CCTAATCATG TTCTTACAAT GGTTTACTAT CTGCTCATAG ACAACCCATC
1801 TGTCATTGGA TTTTCTTAAA ATCTGAACTT CATCGAAACT CTCATCTATA
1851 AACCATCTCA CTTACACTAT TTAAGTAGAT TCCTAGTTTA TAGTTATAT

FIG. 8

Bovine RSV F-protein gene
LOCUS      7308    1902 bp
DEFINITION 7308    1902 bp, 1902 bases, 96AE3B09 checksum.
ORIGIN
```
   1 GGGGCAAATA AGGATGGCGA CAACAGCCAT GAGGATGATC ATCAGCATTA
  51 TCTTCATCTC TACCTATGTG ACACATATCA CTTTATGCCA AAACATAACA
 101 GAAGAATTTT ATCAATCAAC ATGCAGTGCA GTTAGTAGAG GTTACCTTAG
 151 TGCATTAAGA ACTGGATGGT ATACAAGTGT GGTAACAATA GAGTTGAGCA
 201 AAATACAAAA AAATGTGTGT AAAAGTACTG ATTCAAAAGT GAAATTAATA
 251 AAGCAAGAAC TAGAAAGATA CAACAATGCA GTAGTGGAAT TGCAGTCACT
 301 TATGCAAAAT GAACCGGCCT CCTTCAGTAG AGCAAAAAGA GGGATACCAG
 351 AGTTGATACA TTATACAAGA AACTCTACAA AAAAGTTTTA TGGGCTAATG
 401 GGCAAGAAGA GAAAAAGGAG ATTTTTAGGA TTCTTGCTAG GTATTGGATC
 451 TGCTGTTGCA AGTGGTGTAG CAGTGTCCAA AGTACTACAC CTGGAGGGAG
 501 AGGTGAATAA AATTAAAAAT GCACTGCTAT CCACAAATAA AGCAGTAGTT
 551 AGTCTATCCA ATGGAGTTAG TGTCCTTACT AGCAAAGTAC TTGATCTAAA
 601 GAACTATATA GACAAAGAGC TTCTACCTCA AGTTAACAAT CATGATTGTA
 651 GGATATCCAA CATAGAAACT GTGATAGAAT CCAACAAAA AAACAATAGA
 701 TTGTTAGAAA TTGCTAGGGA ATTTAGTGTA AATGCTGGTA TTACCACACC
 751 TCTCAGTACA TACATGTTGA CCAATAGTGA ATTACTATCA CTAATTAATG
 801 ATATGCCTAT AACGAATGAC CAAAAAAAGC TAATGTCAAG TAATGTTCAA
 851 ATAGTCAGGC AACAGAGTTA TTCCATTATG TCAGTGGTCA AAGAAGAAGT
 901 CATAGCTTAT GTTGTACAAT GCCTATTTA TGGAGTTATA GACACCCCCT
 951 GTTGGAAACT ACACACCTCT CCGTTATGCA CCACTGATAA TAAAGAAGGG
1001 TCAAACATCT GCTTAACTAG GACAGATCGT GGGTGGTATT GTGACAATGC
1051 AGGCTCTGTG TCTTTTTTCC CACAGACAGA GACATGTAAG GTACAATCAA
1101 ATAGAGTGTT CTGTGACACA ATGAACAGTT TAACTCTGCC TACTGACGTT
1151 AACTTATGCA ACACTGACAT ATTCAATACA AAGTATGACT GTAAAATAAT
1201 GACATCTAAA ACTGACATAA GTAGCTCTGT GATAACTTCA ATTGGAGCTA
1251 TTGTATCATG CTATGGGAAG ACAAAATGTA CAGCTTCTAA TAAAAATCGT
1301 GGAATCATAA AGACTTTTTC AATGGGTGT GATTATGTAT CAAACAAAGG
1351 AGTAGATACT GTATCTGTTG GTAACACACT ATATTATGTA AATAAGCTAG
1401 AGGGGAAAGC ACTCTATATA AAGGGTGAAC CAATTATTAA TTACTATGAT
1451 CCACTAGTGT TTCCTTCTGA TGAGTTTGAT GCATCAATTG CCCAAGTAAA
1501 CGCAAAAATA AACCAAAGCC TGGCCTTCAT ACGTCGATCT GATGAGTTAC
1551 TTCACAGTGT AGATGTAGGA AAATCCACCA CAAATGTAGT AATTACTACT
1601 ATTATCATAG TGATAGTTGT AGTGATATTA ATGTTAATAG CTGTAGGATT
1651 ACTGTTTTAC TGTAAGACCA AGAGTACTCC TATCATGTTA GGGAAGGATC
1701 AGCTCAGTGG TATCAACAAT CTTTCCTTTA GTAAATGAAA TGCATAATGT
1751 TTACAATCTA AACCTCAGAA TCATAAATGT GATGAGCTAA ATTTACTAAT
1801 ACATTCAAAA GTTCTATCCG CCAAGACCTG CATTTTTATC AGGTCTTACA
1851 TAAGCTAACC TTACATGCTA CACTCAACTC CATGTTGATA GTTATATAAA
1901 AA
```

Human RSV G-protein gene
LOCUS    7818    918 bp
DEFINITION  7818    918 bp, 918 bases, D91603F4 checksum.
ORIGIN
```
   1 GGGGCAAATG CAAACATGTC CAAAAACAAG GACCAACGCA CCGCTAAGAC
  51 ATTAGAAAGG ACCTGGGACA CTCTCAATCA TTTATTATTC ATATCATCGT
 101 GCTTATATAA GTTAAATCTT AAATCTGTAG CACAAATCAC ATTATCCATT
 151 CTGGCAATGA TAATCTCAAC TTCACTTATA ATTGCAGCCA TCATATTCAT
 201 AGCCTCGGCA AACCACAAAG TCACACCAAC AACTGCAATC ATACAAGATG
 251 CAACAAGCCA GATCAAGAAC ACAACCCCAA CATACCTCAC CCAGAATCCT
 301 CAGCTTGGAA TCAGTCCCTC TAATCCGTCT GAAATTACAT CACAAATCAC
 351 CACCATACTA GCTTCAACAA CACCAGGAGT CAAGTCAACC CTGCAATCCA
 401 CAACAGTCAA GACCAAAAAC ACAACAACAA CTCAAACACA ACCCAGCAAG
 451 CCCACCACAA AACAACGCCA AAACAAACCA CCAAGCAAAC CCAATAATGA
 501 TTTTCACTTT GAAGTGTTCA ACTTTGTACC CTGCAGCATA TGCAGCAACA
 551 ATCCAACCTG CTGGGCTATC TGCAAAAGAA TACCAAACAA AAAACCAGGA
 601 AAGAAAACCA CTACCAAGCC CACAAAAAAA CCAACCCTCA AGACAACCAA
 651 AAAAGATCCC AAACCTCAAA CCACTAAATC AAAGGAAGTA CCCACCACCA
 701 AGCCCACAGA AGAGCCAACC ATCAACACCA CCAAAACAAA CATCATAACT
 751 ACACTACTCA CCTCCAACAC CACAGGAAAT CCAGAACTCA CAAGTCAAAT
 801 GGAAACCTTC CACTCAACTT CCTCCGAAGG CAATCCAAGC CCTTCTCAAG
 851 TCTCTACAAC ATCCGAGTAC CCATCACAAC CTTCATCTCC ACCCAACACA
 901 CCACGCCAGT AGTTACTT
```

Bovine RSV G-protein gene
LOCUS    6939    840 bp
DEFINITION  6939    840 bp, 840 bases, 627DFBCE checksum.
ORIGIN
```
   1 GGGGCAAATA CAAGTATGTC CAACCATACC CACCATCTTA AATTCAAGAC
  51 ATTAAAGAGG GCTTGGAAAG CCTCAAAATA CTTCATAGTA GGATTATCAT
 101 GTTTATATAA GTTCAATTTA AAATCCCTTG TCCAAACGGC TTTGACCACC
 151 TTAGCAATGA TAACCTTGAC ATCACTCGTC ATAACAGCCA TTATTTACAT
 201 TAGTGTGGGA AATGCTAAAG CCAAGCCCAC ATCCAAACCA ACCATCCAAC
 251 AAACACAACA GCCCCAAAAC CATACCTCAC CATTTTTCAC AGAGCACAAC
 301 TACAAATCAA CTCACACATC AATTCAAAGC ACCACACTGT CCCAACTACC
 351 AAACACAGAC ACCACTAGAG AAACTACATA CAGTCACTCA ATCAACGAAA
 401 CCCAAAACAG AAAAATCAAA AGCCAATCCA CTCTACCCGC CACCAGAAAA
 451 CCACCAATTA ACCCATCGGG AAGCAACCCC CCTGAAAACC ACCAAGACCA
 501 CAACAACTCC CAAACACTCC CCTATGTGCC TTGCAGTACA TGTGAAGGTA
 551 ATCTTGCTTG TTTATCACTC TGCCAAATCG GGCGGAGAG AGCACCAAGC
 601 AGAGCCCCTA CAATCACCCT CAAAAAGACT CCAAAACCCA AACCACCAA
 651 AAAGCCAACC AAGACAACAA TCCACCACAG AACCAGCCCT GAAGCCAAAC
 701 TGCAACCCAA AAACAACACG GCAGCTCCAC AACAAGGCAT CCTCTCTTCA
 751 CCAGAACACC ACACAAATCA ATCAACTACA CAGATCTAAC AACACACCTC
 801 CATATAATAT CAATTATGTT CATATATAGT TATTTAAAAA
```

FIG. 11

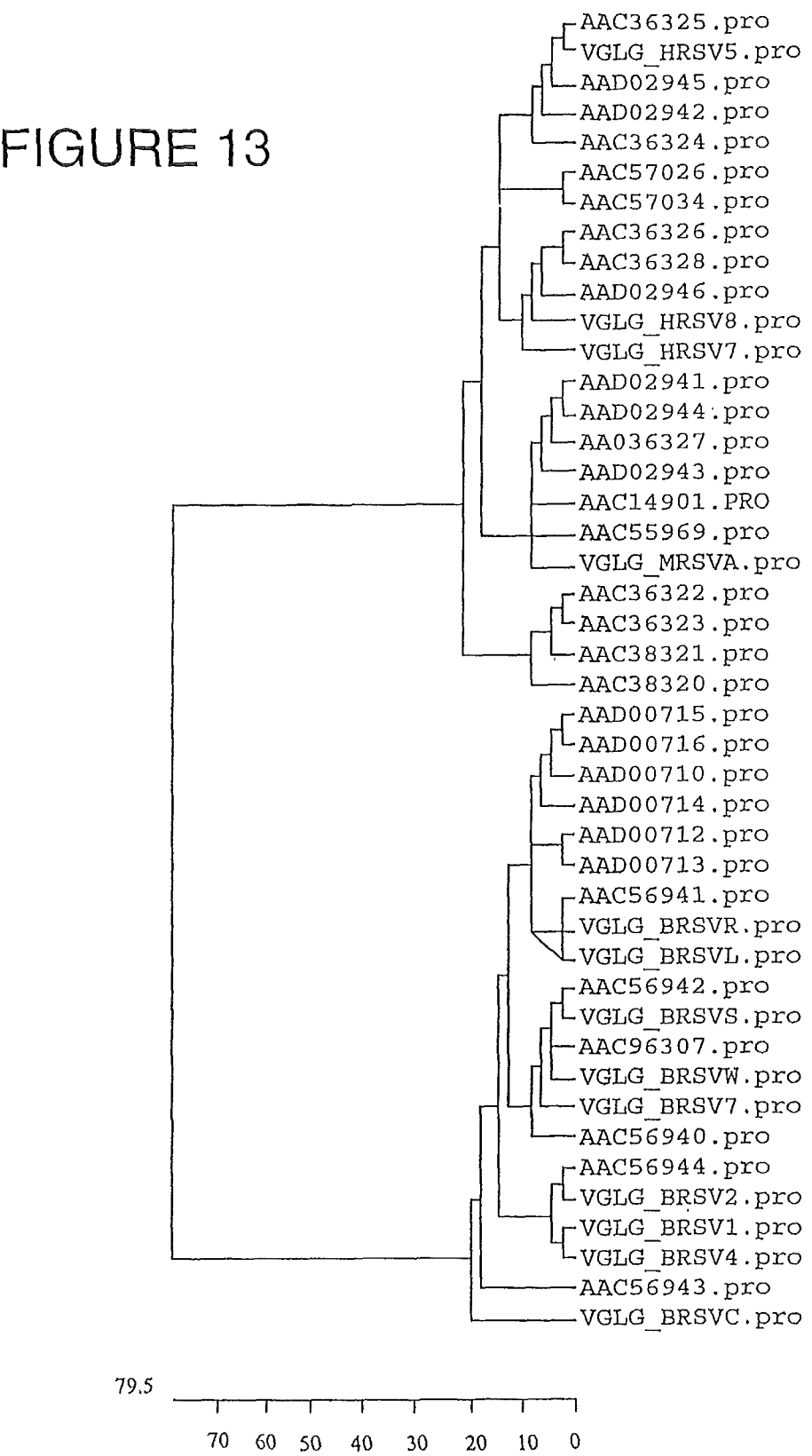

SEQUENCE LISTING

<160> NUMBER OF SEQ ID NOS: 7

<210> SEQ ID NO 1
<211> LENGTH: 1899
<212> TYPE: DNA
<213> ORGANISM: Human respiratory syncytial virus

<400> SEQUENCE: 1

```
ggggcaaata acaatggagt tgctaatcct caaagcaaat gcaattacca caatcctcac      60
tgcagtcaca ttttgttttg cttctggtca aaacatcact gaagaatttt atcaatcaac     120
atgcagtgca gttagcaaag gctatcttag tgctctgaga actggttggt ataccagtgt     180
tataactata gaattaagta atatcaagga aaataagtgt aatggaacag atgctaaggt     240
aaaattgata aaacaagaat tagataaata taaaaatgct gtaacagaat tgcagttgct     300
catgcaaagc acaccaccaa caaacaatcg agccagaaga gaactaccaa ggtttatgaa     360
ttatacactc aacaatgcca aaaaaccaa tgtaacatta agcaagaaaa ggaaaagaag     420
atttcttggt tttttgttag gtgttggatc tgcaatcgcc agtggcgttg ctgtatctaa     480
ggtcctgcac ctagaagggg aagtgaacaa gatcaaaagt gctctactat ccacaaacaa     540
ggctgtagtc agcttatcaa atggagttag tgtcttaacc agcaaagtgt tagacctcaa     600
aaactatata gataaacaat tgttacctat tgtgaacaag caaagctgca gcatatcaaa     660
tatagaaact gtgatagagt tccaacaaaa gaacaacaga ctactagaga ttaccaggga     720
atttagtgtt aatgcaggtg taactacacc tgtaagcact tacatgttaa ctaatagtga     780
attattgtca ttaatcaatg atatgcctat aacaaatgat cagaaaaagt taatgtccaa     840
caatgttcaa atagttagac agcaaagtta ctctatcatg tccataataa agaggaagt     900 cttagcatat gtagtacaat taccactata tggtgttata gatacaccct gttggaaact     960
acacacatcc cctctatgta caaccaacac aaaagaaggg tccaacatct gtttaacaag    1020
aactgacaga ggatggtact gtgacaatgc aggatcagta tctttcttcc cacaagctga    1080
aacatgtaaa gttcaatcaa atcgagtatt ttgtgacaca atgaacagtt taacattacc    1140
aagtgaaata aatctctgca atgttgacat attcaacccc aaatatgatt gtaaaattat    1200
gacttcaaaa acagatgtaa gcagctccgt tatcacatct ctaggagcca ttgtgtcatg    1260
ctatggcaaa actaaatgta cagcatccaa taaaaatcgt ggaatcataa agacttttc    1320 taacgggtgc gattatgtat caaataaagg gatggacact gtgtctgtag taacacatt    1380 atattatgta aataagcaag aaggtaaaag tctctatgta aaaggtgaac caataataaa    1440
tttctatgac ccattagtat tcccctctga tgaatttgat gcatcaatat ctcaagtcaa    1500
cgagaagatt aaccagagcc tagcatttat tcgtaaatcc gatgaattat tacataatgt    1560
aaatgctggt aaatccacca caaatatcat gataactact ataattatag tgattatagt    1620
aatattgtta tcattaattg ctgttggact gctcttatac tgtaaggcca gaagcacacc    1680
agtcacacta agcaaagatc aactgagtgg tataaataat attgcattta gtaactaaat    1740
aaaaatagca cctaatcatg ttcttacaat ggtttactat ctgctcatag acaacccatc    1800
```

| | |
|---|---|
| tgtcattgga ttttcttaaa atctgaactt catcgaaact ctcatctata aaccatctca | 1860 |
| cttacactat ttaagtagat tcctagttta tagttatat | 1899 |

<210> SEQ ID NO 2
<211> LENGTH: 1902
<212> TYPE: DNA
<213> ORGANISM: Bovine respiratory syncytial virus

<400> SEQUENCE: 2

| | |
|---|---|
| ggggcaaata aggatggcga caacagccat gaggatgatc atcagcatta tcttcatctc | 60 |
| tacctatgtg acacatatca ctttatgcca aaacataaca gaagaatttt atcaatcaac | 120 |
| atgcagtgca gttagtagag gttaccttag tgcattaaga actggatggt atacaagtgt | 180 |
| ggtaacaata gagttgagca aaatacaaaa aaatgtgtgt aaaagtactg attcaaaagt | 240 |
| gaaattaata aagcaagaac tagaaagata caacaatgca gtagtggaat tgcagtcact | 300 |
| tatgcaaaat gaaccggcct ccttcagtag agcaaaaaga gggataccag agttgataca | 360 |
| ttatacaaga aactctacaa aaaagtttta tgggctaatg ggcaagaaga gaaaaaggag | 420 |
| attttttagga ttcttgctag gtattggatc tgctgttgca agtggtgtag cagtgtccaa | 480 |
| agtactacac ctggagggag aggtgaataa aattaaaaat gcactgctat ccacaaataa | 540 |
| agcagtagtt agtctatcca atggagttag tgtccttact agcaaagtac ttgatctaaa | 600 |
| gaactatata gacaaagagc ttctacctca agttaacaat catgattgta ggatatccaa | 660 |
| catagaaact gtgatagaat tccaacaaaa aacaataga ttgttagaaa ttgctaggga | 720 |
| atttagtgta aatgctggta ttaccacacc tctcagtaca tacatgttga ccaatagtga | 780 |
| attactatca ctaattaatg atatgcctat aacgaatgac caaaaaaagc taatgtcaag | 840 |
| taatgttcaa atagtcaggc aacagagtta ttccattatg tcagtggtca agaagaagt | 900 |
| catagcttat gttgtacaat tgcctatttta tggagttata gacaccccct gttggaaact | 960 |
| acacacctct ccgttatgca ccactgataa taaagaaggg tcaaacatct gcttaactag | 1020 |
| gacagatcgt gggtggtatt gtgacaatgc aggctctgtg tcttttttcc cacagacaga | 1080 |
| gacatgtaag gtacaatcaa atagagtgtt ctgtgacaca atgaacagtt taactctgcc | 1140 |
| tactgacgtt aacttatgca acactgacat attcaataca aagtatgact gtaaaataat | 1200 |
| gacatctaaa actgacataa gtagctctgt gataacttca attggagcta ttgtatcatg | 1260 |
| ctatgggaag acaaaatgta cagcttctaa taaaaatcgt ggaatcataa agactttttc | 1320 |
| caatgggtgt gattatgtat caaacaaagg agtagatact gtatctgttg gtaacacact | 1380 |
| atattatgta aataagctag agggaaaagc actctatata aagggtgaac caattattaa | 1440 |
| ttactatgat ccactagtgt ttccttctga tgagtttgat gcatcaattg cccaagtaaa | 1500 |
| cgcaaaaata aaccaaagcc tggccttcat acgtcgatct gatgagttac ttcacagtgt | 1560 |
| agatgtagga aaatccacca caaatgtagt aattactact attatcatag tgatagttgt | 1620 |
| agtgatatta atgttaatag ctgtaggatt actgttttac tgtaagacca agagtactcc | 1680 |
| tatcatgtta gggaaggatc agctcagtgg tatcaacaat cttccttta gtaaatgaaa | 1740 |
| tgcataatgt ttacaatcta aacctcagaa tcataaatgt gatgagctaa atttactaat | 1800 |
| acattcaaaa gttctatccg ccaagacctg cattttatc aggtcttaca taagctaacc | 1860 |
| ttacatgcta cactcaactc catgttgata gttatataaa aa | 1902 |

<210> SEQ ID NO 3
<211> LENGTH: 918
<212> TYPE: DNA

<213> ORGANISM: Human respiratory syncytial virus

<400> SEQUENCE: 3

```
ggggcaaatg caaacatgtc caaaaacaag gaccaacgca ccgctaagac attagaaagg      60
acctgggaca ctctcaatca tttattattc atatcatcgt gcttatataa gttaaatctt     120
aaatctgtag cacaaatcac attatccatt ctggcaatga atctcaac ttcacttata      180
attgcagcca tcatattcat agcctcggca aaccacaaag tcacaccaac aactgcaatc     240
atacaagatg caacaagcca gatcaagaac acaaccccaa catacctcac ccagaatcct     300
cagcttggaa tcagtccctc taatccgtct gaaattacat acaaatcac caccatacta      360
gcttcaacaa caccaggagt caagtcaacc ctgcaatcca acagtcaa gaccaaaaac       420
acaacaacaa ctcaaacaca cccagcaag cccaccacaa acaacgcca aaacaaacca       480
ccaagcaaac ccaataatga ttttcacttt gaagtgttca actttgtacc ctgcagcata     540
tgcagcaaca atccaacctg ctgggctatc tgcaaaagaa taccaaacaa aaaaccagga    600
aagaaaacca ctaccaagcc cacaaaaaaa ccaaccctca agacaaccaa aaaagatccc    660
aaacctcaaa ccactaaatc aaaggaagta cccaccacca gcccacaga gagccaacc      720
atcaacacca ccaaaacaaa catcataact acactactca cctccaacac cacaggaaat    780
ccagaactca aagtcaaat ggaaaccttc cactcaactt cctccgaagg caatccaagc     840
ccttctcaag tctctacaac atccgagtac ccatcacaac cttcatctcc acccaacaca    900
ccacgccagt agttactt                                                  918
```

<210> SEQ ID NO 4
<211> LENGTH: 840
<212> TYPE: DNA
<213> ORGANISM: Bovine respiratory syncytial virus

<400> SEQUENCE: 4

```
ggggcaaata caagtatgtc caaccatacc caccatctta aattcaagac attaaagagg      60
gcttggaaag cctcaaaata cttcatagta ggattatcat gtttatataa gttcaattta     120
aaatcccttg tccaaacggc tttgaccacc ttagcaatga taaccttgac atcactcgtc     180
ataacagcca ttatttacat tagtgtggga aatgctaaag ccaagcccac atccaaacca     240
accatccaac aaacacaaca gccccaaaac catacctcac cattttcac agagcacaac     300
tacaaatcaa ctcacacatc aattcaaagc accacactgt cccaactacc aaacacagac     360
accactagag aaaactacata cagtcactca atcaacgaaa cccaaaacag aaaaatcaaa    420
agccaatcca ctctacccgc caccagaaaa ccaccaatta acccatcggg aagcaacccc    480
cctgaaaacc accaagacca caacaactcc caaacactcc cctatgtgcc ttgcagtaca    540
tgtgaaggta atcttgcttg tttatcactc tgccaaatcg ggccggagag agcaccaagc    600
agagccccta caatcaccct caaaaagact ccaaaaccca aaccaccaa aaagccaacc    660
aagacaacaa tccaccacag aaccagccct gaagccaaac tgcaacccaa aaacaacacg    720
gcagctccac aacaaggcat cctctcttca ccagaacacc acacaaatca atcaactaca    780
cagatctaac aacacacctc catataatat caattatgtt catatatagt tatttaaaaa    840
```

<210> SEQ ID NO 5
<211> LENGTH: 35
<212> TYPE: DNA
<213> ORGANISM: Primer

<400> SEQUENCE: 5

-continued

```
cacgcggccg ctaacaatgg agttgctaat cctca                              35

<210> SEQ ID NO 6
<211> LENGTH: 33
<212> TYPE: DNA
<213> ORGANISM: Primer

<400> SEQUENCE: 6
cacgagctct ttatttagtt actaaatgca ata                                33

<210> SEQ ID NO 7
<211> LENGTH: 71
<212> TYPE: DNA
<213> ORGANISM: Primer

<400> SEQUENCE: 7
cactctagag tttttatttt taattttctt tcaaatactt ccatcatgga gtgctaatcc   60
tcaaagcaaa t                                                        71
```

PLANT-DERIVED VACCINES AGAINST RESPIRATORY SYNCYTIAL VIRUS

INTRODUCTION

The present application is a continuation of U.S. Ser. No. 12/847,401 filed Jul. 30, 2010, now abandoned, which is a continuation of U.S. Ser. No. 10/947,211, filed Sep. 23, 2004, now abandoned, which is a continuation of U.S. Ser. No. 09/568,018 filed May 10, 2000, now abandoned, and claims benefit of U.S. Provisional Application No. 60/133,536, filed May 11, 1999, each of which are herein incorporated by reference in their entireties.

FIELD OF THE INVENTION

The present invention generally relates to vaccines against respiratory syncytial virus (RSV) and to plant-derived vaccines against RSV. The vaccines may be used prophylatically and/or therapeutically to treat RSV infection.

BACKGROUND OF THE INVENTION

Respiratory syncytial virus (RSV) is an RNA virus of the genus Pneumovirus containing two main antigenic glycoproteins, F and G (1). Additional structural proteins include a major nucleocapsid protein (N), a nucleocapsid phosphoprotein (P), a large nucleocapsid protein (L), an envelope matrix protein (M), and a glycoprotein (22,000 daltons) (138). A virally encoded protein of about 9,500 daltons and other small proteins are also known to be in infected cells (138). Infections with RSV are referable to all segments of the respiratory tract, and are usually associated with fever, cough, runny nose and fatigue. This virus is a major human pathogen and a leading cause of bronchiolitis and pneumonia in infants, children, adults and the elderly (1). A major difficulty in developing an effective RSV vaccine has been the fact that natural infection confers, at most, only temporary protection against the disease (1).

Prior to the present invention, only one RSV vaccine administered parenterally (10) had been used. This vaccine exacerbated RSV disease and was withdrawn from use (10). A number of live attenuated forms of RSV have been proposed for treatment of RSV infection (87, 89). However, there are limitations imposed by such approaches. For example, live infection does not provide full immunity and single point mutations may revert to wild type with undesirable consequences.

A need exists for a better way to treat RSV. The present invention is directed to a new approach to achieve this objective.

SUMMARY OF THE INVENTION

The present invention is directed to highly effective RSV vaccines that overcome some of the deficiencies of conventional RSV vaccines. In particular, the present invention is directed to plant-derived RSV vaccines developed by introducing RSV nucleotide sequences into transgenic plants.

The invention thus provides novel chimeric nucleic acid constructs that contain a nucleotide sequence adapted for protein expression in plants and an RSV coding sequence.

The invention also provides a method for the expression of the RSV nucleotide sequences in plant cells and plants.

The invention thus provides transformed plant cells and transgenic plants transformed with the novel chimeric nucleic acid constructs.

The invention also provides extracts of plant cells and transgenic plants transformed with the novel chimeric nucleic acid constructs. The extracts may be used to prepare immunogenic complexes and antigenic compositions useful in prophylactic treatment, therapeutic treatment and diagnosis of RSV disease.

The invention thus provides a method of immunizing a mammal against RSV using the novel immunogenic complexes and antigenic compositions.

The invention also provides diagnostic methods and diagnostic kits for the identification or detection of RSV.

The invention further provides the further enhancement of expression of the RSV nucleotide sequence in plant cells and plants to achieve an antigen titer level sufficient to induce a protective immune response. Methods for further enhanced expression of the RSV nucleotide sequence in plant cells and plants include using enhancer elements and/or untranslated leader sequences in combination with a promoter and/or using plant synthetic nucleotide sequences with optimized codon usage.

The present invention also provides enhanced antibody production by use of an adjuvant with the RSV vaccine. Thus, the RSV nucleotide sequence is expressed in combination with a second substance in order to produce an adjuvant effect to RSV. The second substance may itself be expressed in the plant, e.g., coexpressed with RSV, or it may be administered separately, e.g., parenterally. Examples of adjuvants that can be used in accordance with the invention include monophosphoryl lipid A and alum and mutant forms of bacterial enterotoxins (92). (See also WO Patent No. 9843668.)

Additional advantages of the present invention will be set forth in the description and examples that follow, or may be learned from practicing the invention. These and other advantages may be realized and attained by means of the features, instrumentalities and/or combinations particularly described herein. It is also to be understood that the foregoing general description and the following detailed description are only exemplary and explanatory and are not to be viewed as limiting or restricting the invention as claimed.

The invention itself, together with further advantages, will best be understood by reference to the following detailed description, taken in conjunction with the accompanying drawings.

BRIEF DESCRIPTION OF THE DRAWINGS

FIG. 7B-7E shows the expanded version of FIG. 7A with additional data. Serum and mucosal RSV-F specific antibody titers from mice fed transgenic or control tomatoes. Triplicate samples were serially diluted and measured by ELISA. End-point titers are plotted (mean±SE) on a linear scale of the dilution factor. (B) RSV-F specific serum IgG and IgA titers from samples collected prior to oral immunization (preimmune) and, on day 32, from control (fed wild-type tomato) and immunized mice (fed transgenic tomatoes). (C) RSV-F specific serum IgG and IgA and mucosal (small intestine) IgA titers from samples collected form the same mice on day 39 after intramuscular injection (boost) on day 33 with inactivated RSV antigen. *$P \leq 0.05$ vs. the immunized serum IgG and IgA samples. (D) RSV-F specific serum titers of the three IgG sub-classes ($IgG_{2a}$, $IgG_{2b}$, and $IgG_1$) from samples collected on day 32 from control and orally-immunized mice. (E) RSV-F specific serum titers of the three IgG sub-classes from samples collected on day 39 from control mice and those boosted with inactivated RSV. *$P \leq 0.05$ vs. the post-boost serum $IgG_1$.

FIG. 8 shows the nucleotide sequence for human RSV-F (strain A2) (26) (SEQ ID NO:1).

FIG. 9 shows the nucleotide sequence for bovine RSV-F (strain ATue51908) (137) (SEQ ID NO:2).

FIG. 10 shows the nucleotide sequence for human RSV-G (strain A2) (95) (SEQ ID NO:3).

FIG. 11 shows the nucleotide sequence for bovine RSV-G (strain ATue51908) (137) (SEQ ID NO:4).

FIG. 13 shows a phylogenetic tree of 44 full-length G protein sequences from the Genbank database. The sequences were aligned using the Clustal V algorithm (Higgins, D. G. & Sharp, P. M.; 1989). Fast and sensitive multiple sequence alignments on a microcomputer. *CABIOS* 5 no, 2: 151-153) via the DNASTAR analysis software, applying the default values. This algorithm produces a value for similarity based upon both absolute amino-acid sequence conservation and evolutionary conservation using the PAM250 weighting table. The X-axis is in units of substitution events. Protein sequence names refer to the Genbank accession numbers. The following sequences are BRSV G proteins: AAD00715, AAD00716, AAD00710, AAD00714, AAD00712, AAD00713, AAC56941, VGLV_BRSVR, VGLG_BRSVL, AAC56942, VGLG_BRSVS, AAC96307, VGLG_BRSVW, VGLG_BRSV7, AAC56940, AAC56944, VGLV_BRSV2, VGLG_BRSV1, VGLV_BRSV4, AAC56943, VGLG_BRSVC.

DETAILED DESCRIPTION OF THE INVENTION

Figure 1:
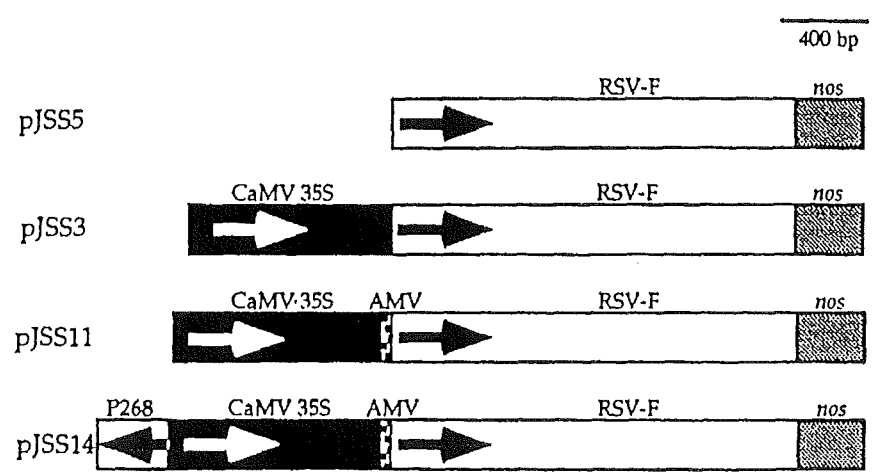
FIG. 1 shows chimeric nucleic acid constructs containing RSV-F nucleotide coding sequence, CaMV 35S promoter, AMV leader, P268 enhancer, and nos terminator used for PEG-mediated protoplast transfection. The name of the plasmid is given on the left. Arrows indicate the orientation of the inserts.

As used herein, an "antigen" is a macromolecule capable of stimulating an immune response upon introduction into a mammal, including humans (hereafter collectively referred to as mammals). As used in this application, antigen means an antigen per se, an antigenic determinant of an antigen, or a fusion protein containing an antigen or antigenic determinant sometimes referred to as native epitopes.

An "antigenic determinant" is a small chemical complex that determines the specificity of an immune response.

An "antigenic protein or peptide of RSV" is a derivative of the structural protein of RSV having sufficient antigenic capacity to produce effective immunologic protection to mammals exposed to RSV.

A "chimeric nucleic acid construct", "nucleic acid" and the like is a polynucleotide that encodes a polypeptide, which may include introns, marker genes, signal sequences, regulatory elements, such as promoters, enhancers and termination sequences, and the like.

"Oral delivery", "oral administration" and the like is the administration of any plant material that can be delivered orally and directly ingested by mammals or other animals. This term is intended to include raw plant material that may be administered orally directly to mammals or other animals or processed plant material that is administered orally to mammals or other animals.

"Eliciting antibodies" is the generation of an immune reaction specific for the cognate complete protein.

An "expression vector" is a plasmid, viral vector or artificial chromosome capable of transforming the genetic composition of eukaryotic cells, e.g., plant cells and plant tissues.

An "immune response" involves the in vivo production of antibodies, also called immunoglobulins, in response to an antigen. This term is intended to include stimulation of T cell activation and cellular immune responses in general, and encompasses the production of circulating as well as secretory antibodies.

An "immunogenic agent" is any antigen capable of eliciting an immune response in animals upon oral ingestion of a eukaryotically expressed antigen. An "antigenic composition" contains one or more immunogenic agents, optionally in combination with a carrier, adjuvant, or the like. Immunogenic agents include antigenically related protein or peptide sequences having an amino acid sequence modified by at least one amino acid, which retain biological characteristics, e.g., antigen specificity and high affinity, of the unmodified sequence as determined, for example, by reacting the protein or peptide sequence with labelled primary monoclonal antibody or secondary antibody against the respective RSV protein and detecting the presence of label by methods such as ELISA, Western blotting techniques or immunoprecipitation.

An "immunogenic complex" is a plant cell or transgenic plant in which a chimeric nucleic acid construct of the invention is introduced; an RSV nucleic acid coding sequence of the invention is expressed; and antigen is produced.

A "nucleotide sequence adapted for protein expression in plants" is a sequence that enables and/or enhances expression of a foreign nucleotide sequence in plants and includes plant regulatory sequences such as promoters, enhancers, termination sequences and the like, as well as plant optimized codon sequences.

An "immunogenically effective amount" is an amount that can achieve an antibody titer level sufficient to immunize a mammal when administered in a mammal.

A coding sequence and a regulatory sequence are "operably joined" when they are covalently linked in such a way as to place the expression or transcription of the coding sequence under the influence or control of the regulatory sequence.

A "respiratory syncytial coding sequence" is a nucleotide sequence capable of coding an RSV protein, peptide or derivative thereof each of which is capable of eliciting antibodies.

"RSV protein" includes RSV-F, RSV-G, RSV-N, RSV-P, RSV-L, 22 K protein, and 9.5 K protein. ((138) See also World Patent No. 8704185 and U.S. Pat. No. 5,149,650).

A "secretory immune response" involves the formation and production of secretory IgA antibodies in secretions that bathe the mucosal surfaces of mammals and in secretions from secretory glands. Secretory immunity is also sometimes referred to as mucosal immunity.

Respiratory syncytial virus (RSV) is an enveloped virus of the Genus Pneumovirus (1). It infects virtually all children worldwide and is the most important pathogen of infancy and early childhood and a major cause of serious lower respiratory tract diseases (1). Surveys of children hospitalized with RSV show mortality rates of 0.1-2.5% (2, 3). Re-infection with RSV is also common and can occur throughout life because natural infection confers only temporary protection against the disease (4). In recent years, RSV infections have been increasingly noted in nursing homes and other group settings serving the institutionalized elderly (1, 5, 6), with pneumonia developing in up to two thirds of the patients (7).

Early attempts to use formalin-inactivated RSV (FI-RSV) administered parenterally as a vaccine resulted in more severe lower respiratory tract disease and higher mortality rates in response to RSV infection in immunized children than non-immunized children (9). Analysis of the immune responses of the two groups to RSV infection showed that a single immunization with FI-RSV administered parenterally resulted in the recruitment of large numbers of eosinophils to infected lung tissues, which led to inflammatory responses. In contrast, prior infection with RSV often produced a cellular immune response that cleared RSV from the lung with little inflammation (10). The response induced by FI-RSV is characteristic of a type 2 T-helper cell (Th2) response and that induced by a replicating virus is typical of a type 1 T-helper cell (Th1) response (11). Th2-type responses usually result from presentation of extracellular antigens by a major histocompatability complex (MHC) class II pathway. Th1-type responses are primed by the presentation of intracellular antigens by a MHC class I pathway, for example, RSV proteins synthesized de novo in infected cells. The choice of antigen presentation pathway is also influenced by the intrinsic affinity of the antigen for a specific class of MHC molecules, the dose of antigen, the adjuvant, and the route of immunization (12).

Prior approaches for treating RSV involve administering RSV antibody parenterally, e.g., by intramuscular injection (59) and by intravenous infusion (60). Although these methods reduce hospitalization by about 50%, each requires multiple administration. Another approach focuses on alleviating the severity of RSV once the infection has occurred by administering a synthetic nucleoside as a small particle aerosol in a hospital setting (61). Different degrees of effectiveness have been observed for this method.

Additional approaches include preparation of RSV protein, peptides and derivatives thereof and administration of the RSV protein, peptides and derivatives thereof parenterally.

World Patent No. 9711177 discloses neutralizing human monoclonal antibodies, fragments and chimeras thereof of RSV.

World Patent No. 9614418 discloses G protein amino acid sequence 130-230.

World Patent No. 9903987 discloses antibodies directed against an epitope of RSV-G corresponding to a sequence selected among one of the peptide sequences included respectively between amino acid residues 150-159, 176-189, 194-207 and 155-176 of the entire sequence of RSV-G, A or B, or of sequences having 98% homology.

World Patent No. 8704185 discloses vaccines for human RSV that can be administered parenterally. The vaccines are prepared by expressing recombinant DNA in a host selected from bacteria, yeast and eukaryote cell cultures of insect or mammalian origin.

World Patent No. 9201471 discloses vaccines for bovine RSV that can be administered parenterally. The vaccines are prepared by expressing recombinant DNA in a host selected from bacteria, yeast and eukaryote cell cultures of insect or mammalian origin.

World Patent No. 9819704 discloses the use of human monoclonal antibodies specific for the F protein of RSV to treat or prevent infection.

Prior to the present invention, the use of transgenic plant cells or transgenic plants had not been employed to prepare plant-derived vaccines.

RSV initiates disease by interaction with mucosal surfaces. Secretory IgA (sIgA) antibodies directed against specific virulence determinants of infecting organisms play an important role in overall mucosal immunity. In many cases, it is possible to prevent the initial infection of mucosal surfaces by stimulating production of mucosal sIgA levels directed against relevant virulence determinants of an infecting organism. Thus, secretory IgA may prevent the initial interaction of RSV with the mucosal surface by blocking attachment and/or colonization, neutralizing surface acting toxins, or preventing invasion of the host cells.

Parenterally administered inactivated whole-cell and whole-virus preparations are effective at eliciting protective serum IgG and delayed type hypersensitivity reactions against organisms that have a significant serum phase in their pathogenesis (e.g., *Salmonella typhi*, Hepatitis B). However, parenteral vaccines are not effective at eliciting mucosal sIgA responses.

Oral immunization can be effective for induction of specific sIgA responses if the antigen is presented to the T and B lymphocytes and accessory cells contained within Peyer's patches where preferential IgA, B-cell development is initiated. The Peyer's patches contain helper T(TH)-cells that mediate B-cell isotype switching directly from IgM cells to IgA. B-cells then migrate to the mesenteric lymph nodes and undergo differentiation, enter the thoracic duct, the general circulation, and subsequently seed all of the secretory tissues of the body, including the lamina propria of the gut and respiratory tract. IgA is then produced by the mature plasma cells, complexed with membrane-bound secretory component, and transported onto the mucosal surface where it is available to interact with invading pathogens. The existence of this common mucosal immune system is a basis for use of live oral vaccines and oral immunization for protection against pathogenic organisms that initiate infection by first interacting with mucosal surfaces.

Oral exposure to particulate and replicating antigen often primes protective immune responses. However, exposure to soluble protein antigens in food most commonly results in immunological tolerance rather than protective immunity (13). Even so, very low doses of soluble protein antigens (less than 5 μg/g of body mass) have been shown to produce systemic responses (13). This phenomenon may be at least partially responsible for the successful elicitation of serum and mucosal immune responses to recombinant antigens in transgenic plants (14-16). Thus, oral immunization with antigens expressed in transgenic plants can be useful against some disease-causing agents (17). Oral delivery of plant-derived antigens or immunogens has produced both serum IgG and mucosal IgA-specific antibodies in mice (14-16) and humans (18). The use of plants for expression and delivery of recombinant proteins is an attractive alternative for developing antigens or immunogens. A major advantage of such vaccines is that they require at most minimal secondary processing prior to use. The use of plants to prepare vaccines of the invention provides other advantages, including the ability to (1) produce antigens destined for vaccine production on a large scale; (2) achieve large biomass cost effectively; (3) utilize many different plant species, thus permitting methods to be employed in many geographical regions; (4) choose different plant tissues (fruit, roots, tubers, etc.) for production; and (5) avoid many of the problems associated with contamination (for example, of fermentors or tissue culture-based systems). Additional advantages include evidence that the presence of plant tissue with an antigen of interest may buffer the antigen from a certain amount of digestive and proteolytic cleavage in the gut; by evidence that plant tissues provide adjuvant-like effects in stimulating or augmenting immune reactions originating in the gut; and by evidence that plant produced RSV protein is glycosylated in planta, which is consistent with the natural protein F and G proteins as detected in infections.

Seven proteins (F, G, N, P, M1 and M2) are present in RSV viruses (138). Glycoproteins exposed on the surface of the RSV envelope are potential candidates as immunogens for development of an RSV vaccine. F and G are the two largest glycoproteins in the envelope. The 90-kDa G glycoprotein is responsible for the initial attachment of RSV to target cells (19). The 68-70 kDa fusion (F) protein enables the lipid membrane of the virus to fuse with the lipid membrane of target cells, thus allowing the viral RNA to be inserted into the target cells (20). Variant RSV strains are known and fall into two main groups, A and B, which differ mainly in the G protein. The F protein, however, is well conserved with 89% amino-acid identity between groups A and B (21). Antibodies to the F protein are cross-reactive between the two groups (22). Immunization of BALB/c mice with recombinant vaccinia viruses expressing the RSV-F protein resulted in the production of neutralizing antibodies (23) that protected against RSV infection (24). Although the F protein was chosen herein for the development of an oral delivery vaccine for RSV, other forms of RSV may also be used to develop an oral delivery vaccine in accordance with the invention (88, 91). Any protein or peptide of RSV that elicits an immune reaction specific for the cognate complete protein may be used, e.g., epitopes (peptides) having 6 or more amino acids may be used. For example, World Patent No. 9819704 discloses the following neutralizing epitopes within the F protein: 205-225; 259-278, 289-299, 417-438 and 483-488; and World Patent No. 9903987 discloses the following neutralizing epitopes within the G protein: 150-159, 155-176, 176-189 and 194-207.

Antibodies selectively bind to an epitope on an RSV protein. Only a small portion of an antibody molecule, the paratope, is involved in the binding of an antibody to its epitope (see Clark, W. R., *The Experimental Foundations of Modern Immunology*, Wiley & Sons (1986). Within the antigen-binding portion of an antibody, as it is well-known in the art, there are complementary determining regions (CDRs), which directly interact with the epitope of the antigen and framework regions (FRs), which maintain the tertiary structure of the paratope. It is well-established that non CDR regions of a mammalian antibody may be replaced with similar regions of conspecific or heterospecific antibodies while retaining the epitope specificity of the original antibody. Thus, it is possible, without undue experimentation, to determine if an RSV protein or peptide sequence related to native RSV has the same specificity as the related native RSV antibody by ascertaining whether the former blocks the latter from binding to RSV. If the antibody being tested competes with native RSV antibody, as shown by a decrease in binding of the native RSV antibody, then it is likely that the two antibodies bind to the same, or a closely related, epitope.

Some exemplary plant functional promoters, which can be used to express a structural nucleotide sequence of the present invention, are among the following (US as used throughout meaning U.S. Patent No.): U.S. Pat. No. 5,352,605 and U.S. Pat. No. 5,530,196—CaMV 35S and 19S promoters; U.S. Pat. No. 5,436,393—patatin promoter; U.S. Pat. No. 5,436,393—a B33 promoter sequence of a patatin gene derived from *Solanum tuberosum*, and which leads to a tuber specific expression of sequences fused to the B33 promoter; WO 94/24298—tomato E8 promoter; U.S. Pat. No. 5,556,653—tomato fruit promoters; U.S. Pat. Nos. 5,614,399 and 5,510,474—a plant ubiquitin promoter system; U.S. Pat. No. 5,824,865—5' cis-regulatory elements of abscisic acid-responsive gene expression; U.S. Pat. No. 5,824,857—promoter from a badnavirus, rice tungro baciliform virus (RTBV); U.S. Pat. No. 5,789,214—a chemically inducible promoter fragment from the 5' flanking region adjacent the coding region of a tobacco PR-1a gene; U.S. Pat. No. 5,783,394—a raspberry drul promoter; WO 98/31812—strawberry promoters and genes; U.S. Pat. No. 5,773,697—promoter is the napin promoter, the phaseolin promoter, and the DC3 promoter; U.S. Pat. No. 5,723,765—a LEA promoter; U.S. Pat. No. 5,723,757—5' transcriptional regulatory region for sink organ specific expression; U.S. Pat. No. 5,723,751-G-box related sequence motifs, specifically lwt and PA motifs, which function as cis-elements of promoters, to regulate the expression of heterologous genes in transgenic plants; U.S. Pat. No. 5,633,440—P119 promoters and their use; U.S. Pat. No. 5,608,144—Group 2 (Gp2) plant promoter sequences; U.S. Pat. No. 5,608,143-nucleic acid promoter fragments derived from several genes from corn, petunia and tobacco; U.S. Pat. No. 5,391,725—promoter sequences were isolated from the nuclear gene for chloroplast GS2 glutamine synthetase and from two nuclear genes for cytosolic GS3 glutamine synthetase in the pea plant, *Pisum sativum*; U.S. Pat. No. 5,378,619-full-length transcript promoter from figwort mosaic virus (FMV); U.S. Pat. No. 5,689,040—an isocitrate lyase promoter; U.S. Pat. No. 5,633,438—a microspore-specific regulatory element; U.S. Pat. No. 5,595,896—expression of heterologous genes in transgenic plants and plant cells using plant asparagine synthetase promoters; U.S. Pat. No. 4,771,002—a promoter region that drives expression of a 1450 base TR transcript in octopine-type crown gall tumors; U.S. Pat. No. 4,962,028—promoter sequences from the gene from the small subunit of ribulose-1,5-bisphosphate carboxylase; U.S. Pat. No. 5,491,288—the *Arabidopsis* histone H4 promoter; U.S. Pat. No. 5,767,363—a seed-specific plant promoter; U.S. Pat. No. 5,023,179—a 21 bp promoter element which is capable of imparting root expression capability to a rbcS-3A promoter, normally a green tissue specific promoter; U.S. Pat. No. 5,792,925—promoters of tissue-preferential transcription of associated DNA sequences in plants, particularly in the roots; U.S. Pat. No. 5,689,053—*Brassica* sp. polygalacturonase promoter; U.S. Pat. No. 5,824,863—a seed coat-specific cryptic promoter region; U.S. Pat. No. 5,689,044—a chemically inducible nucleic acid promoter fragment isolated from the tobacco PR-1a gene is inducible by application of a benzo-1,2,3-thiadiazole, an isonicotinic acid compound, or a salicylic acid compound; U.S. Pat. No. 5,654,414—promoter fragment isolated from a cucumber chitinase/lysozyme gene that is inducible by application of benzo-1,2,3-thiadiazole; U.S. Pat. No. 5,824,872—a constitutive promoter from tobacco that directs expression in at least ovary, flower, immature embryo, mature embryo, seed, stem, leaf and root tissues; U.S. Pat. No. 5,223,419—alteration of gene expression in plants; U.S. Pat. No. 5,290,924—a recombinant promoter for gene expression in monocotyledonous plants; WO 95/21248—method for using TMV to overproduce peptides and proteins; WO 98/05199—nucleic acid comprising shoot meristem-specific promoter and regulated sequence; EP-B-0122791—phaseolin promoter and structural gene; U.S. Pat. No. 5,097,025—plant promoters [sub domain of CaMV 35S]; WO 94/24294—use of tomato E8-derived promoters to express heterologous genes, e.g. 5-adenosylmethionine hydrolase in ripening fruit; U.S. Pat. No. 5,801,027—method of using transactivation proteins to control gene expression in transgenic plants; U.S. Pat. No. 5,821,398-DNA molecules encoding inducible plant promoters and tomato Adh2 enzyme; WO 97/47756—synthetic plant core promoter and upstream regulatory element; U.S. Pat. No. 5,684,239—monocot having dicot wound inducible promoter; U.S. Pat. No. 5,110,732—selective gene expression in plants; U.S. Pat. No. 5,106,739—CaMV 35S enhanced mannopine synthase promoter and method for using the same; U.S. Pat. No. 5,420,034—seed specific transcription regulation; U.S. Pat. No. 5,623,067—seed specific promoter region; U.S. Pat. No. 5,139,954—DNA promoter fragments from wheat; WO 95/14098—chimeric regulatory regions and gene cassettes for use in plants; WO 90/13658—production of gene products to high levels; U.S. Pat. No. 5,670,349-HMG promoter expression system and post harvest production of gene products in plants and plant cell cultures; U.S. Pat. No. 5,712,112—gene expression system comprising the promoter region of the alpha amylase genes in plants.

Some enhancers that can be used with the present invention are among the following: U.S. Pat. No. 5,424,200 and U.S. Pat. No. 5,196,525—CaMV 35S enhancer sequences; U.S. Pat. No. 5,359,142, U.S. Pat. No. 5,322,938, U.S. Pat. No. 5,164,316 and U.S. Pat. No. 5,424,200—tandemly duplicated CaMV 35S enhancers; WO 87/07664-Ω' region of TMV; WO 98/14604—intron 1 and/or intron 2 of the PAT1 gene; U.S. Pat. No. 5,593,874—HSP70 introns that when present in a non-translated leader of a chimeric gene enhance expression in plants; U.S. Pat. No. 5,710,267, U.S. Pat. No. 5,573,932 and U.S. Pat. No. 5,837,849—plant enhancer element capable of being bound by an OCS transcription factor; U.S. Pat. No. 5,290,924—a maize Adh1 intron; JP 8256777—translation enhancer sequence.

A “nucleic acid construct” of the present invention can also include a transcription termination sequence functional in a plant host. Exemplary termination sequences include nopaline synthase (nos) (63), vegetative storage protein (vsp) (64), and proteinase inhibitor-2 (pint) (65) termination sequences.

Constructs (cassettes) of the present invention can be obtained by direct nucleotide synthesis, e.g., using the phosphoramidite method, or they can be assembled from selected regions of other gene reservoirs, such as plasmids. The latter method is preferred whenever the target components are too large to be efficiently synthesized directly. To retrieve a desired nucleotide sequence, promoter, termination sequence, and the like, from a plasmid, synthetic oligonucleotides, PCR, and restriction enzymes are used to assemble the requisite components into the desired cassette, using conventional techniques (66), and as described further herein below.

Also, whenever it is desired to generate a mutation in a peptide of the present invention, site-directed mutagenesis can be employed using conventional techniques, and as described herein below. In this regard, it is worthy to note that a library of mutant peptides, wherein single, double, or higher mutations are generated in the target peptide, can be prepared using random mutagenesis techniques. Mutagenesis techniques are described generally, e.g., in *Current Protocols in Molecular Biology*, Ausubel, F. et al. eds., John Wiley (1998), and random mutagenesis (also referred to as “DNA shuffling”) is the subject of U.S. Pat. Nos. 5,605,793, 5,811,238, 5,830,721, 5,834,252, and 5,837,458 to Stemmer et al.

The present invention also relates to an expression vector for transforming plant cells to express RSV to induce an immune response in animals. Such an expression vector comprises a selectable marker ligated to an aforementioned nucleic acid construct. The vector typically further comprises an *E. coli* origin of replication to facilitate its replication in this microorganism. An expression vector of the invention also usually comprises an *A. tumefaciens* origin of replication, to permit its replication therein, such as when it is to be used for plant transformation. Accordingly, strains of the corresponding microorganisms transfected with a vector of the invention are contemplated.

A plant cell for transformation is preferably one from a plant that can be administered orally readily or can have expressed protein readily isolated. A plant cell for transformation is preferably one from which a mature plant can be developed and grown, and which contains tissues amenable to the delivery in mammals and other animals of antigens for vaccination by oral or mucosal means. Representative plants include tobacco, banana, tomato, carrot and apple. A transgenic plant seed transformed with an aforementioned nucleic acid construct, which is obtained by propagation of a transgenic plant, is yet a further aspect of the invention.

Additionally, the present invention is directed to transformation of plants or plant tissues with synthetic nucleic acid sequences encoding RSV protein where the origin codons have been systematically replaced by plant-preferred codons. This replacement or substitution of plant-preferred codons for the corresponding origin codons enhances the expression of the RSV protein and can facilitate expression of the protein in a particular part, e.g., the fruit or tuber, of the organism.

A transgenic plant or plant part of the invention comprises an aforementioned nucleic acid construct, such as when it is integrated into the nuclear genome of the plant. Although the construct may in some cases be maintained outside the chromosome, such as in the mitochondrion, chloroplast or cytoplasm, the preferred locus is the nuclear genome.

Among the principal methods for effecting transfer of foreign nucleic acid constructs into plants is the *A. tumefaciens* transformation technique. This method is based upon the etiologic agent of crown gall, which afflicts a wide range of dicotyledons and gymnosperms. When the target plant host is susceptible to infection, the *A. tumefaciens* system is generally superior to other methods, vide infra, due to the higher rates of transformation and more predictable chromosome integration patterns.

The *A. tumefaciens* technique involves transfer of a segment of plasmid DNA, called transforming DNA (T-DNA), from *Agrobacterium* to the target plant cell where it integrates into the plant genome. Whenever *A. tumefaciens*-mediated transformation of plants with a nucleic acid construct of the invention is to be employed, it is preferred to further provide flanking T-DNA border regions of *A. tumefaciens*, which bracket the transforming DNA (T-DNA) and signal the polynucleotide that is to be transferred and integrated into the plant genome. Typically, a plasmid vector containing the gene to be transferred is first constructed and replicated in *E. coli*. This vector also contains signal sequences flanking the desired gene, which define the borders of the T-DNA segment that integrates into the plant genome. A selectable marker (such as a gene encoding resistance to an antibiotic such as kanamycin) can also be inserted between the left border (LB) and right border (RB) sequences to permit ready selection of transformed plant cells. The vector in *E. coli* is next transferred to *Agrobacterium*, which can be accomplished via a conjugation mating system or by direct uptake. Once inside the *Agrobacterium*, the vector containing the foreign gene can undergo homologous recombination with a tumor-inducing (Ti) plasmid of the bacterium to incorporate the T-DNA into the Ti plasmid. The Ti plasmids contain a set of inducible virulence (vir) genes that effect transfer of the T-DNA to plant cells. Alternatively, the shuttle vector can be subjected in trans to the vir genes of the Ti plasmids. In a preferred aspect, the Ti plasmids of a given strain are "disarmed", whereby the one genes of their T-DNAs are eliminated or suppressed to avoid formation of tumors in the transformed plant, but their vir genes still effect transfer of T-DNA to the plant host (67, 68).

Much research with the *A. tumefaciens* system now permits routine transformation of a variety of plant tissues (69, 70, 71, 72). Representative plants that have been transformed with this system and representative references are listed in Table 1. Other plants having usable parts, or which can be processed to afford isolated protein, can be transformed by the same methods or routine modifications thereof.

TABLE 1

| Plant | Reference |
| --- | --- |
| Tobacco | Barton, K. et al., (1983) *Cell* 32, 1033 |
| Tomato | Fillatti, J. et al., (1987) *Bio/Technology* 5, 726-730 |
| Potato | Hoekema, A. et al. (1989) *Bio/Technology* 7: 273-278 |
| Eggplant | Filipponee, E. et al. (1989) *Plant Cell Rep.* 8: 370-373 |
| Pepino | Atkinson, R... et al. (1991) *Plant Cell Rep.* 10: 208-212 |
| Yam | Shafer, W. et al. (1987) *Nature*, 327: 529-532 |
| Soybean | Delzer, B. et al. (1990) *Crop Sci.*, 30: 320-322 |
| Pea | Hobbs, S. et al. (1989) *Plant Cell Rep.* 8: 274-277 |
| Sugar beet | Kallerhoff, J. et al. (1990) *Plant Cell Rep..* 9: 224-228 |
| Lettuce | Michelmore, R., et al. (1987) *Plant Cell Rep.* 6: 439-442 |
| Bell pepper | Liu, W. et al. (1990) *Plant Cell Rep.* 9: 3 60-364 |
| Celery | Liu, C-N. et al. (1992) *Plant Mol Biol* 1071-1087 |
| Carrot | Liu, C-N. et al. (1992) *Plant Mol Biol* 1071-1087 |
| Asparagus | Delbriel, B. et al. (1993) *Plant Cell Rep.* 12: 129-132 |
| Onion | Dommisse, E. et al. (1990) *Plant Sci.*, 69: 249-257 |
| Grapevine | Baribault, T., et al. (1989) *Plant Cell Rep.* 8: 137-140 |
| Muskmelon | Fang, G., et al. (1990) *Plant Cell Rep.* 9: 160-164 |
| Strawberry | Nehra, N. et al. (1990) *Plant Cell Rep..* 9: 10-13 |
| Rice | Raineri, D. et al (1990) *Bio/Technology*, 8: 33-38 |
| Sunflower | Schrammeijer, B. et al. (1990) *Plant Cell Rep.* 9: 55-60 |
| Rapeseed/Canola | Pua, B. et al. (1987) *Bio/Technology*, 5, 815 |
| Wheat | Mooney, P. et al. (1991) *Plant Cell, Tiss. Organ Cult.* 25: 209-218 |
| Oats | Donson, J. et al. (1988) *Virology*, 162: 248-250 |
| Maize | Gould, J. et al. (1991) *Plant Physiol.* 95: 426-434 |
| Alfalfa | Chabaud, M. et al. (1988) *Plant Cell Rep.* 7: 512-516 |
| Cotton | Umbeck, P. et al. (1987) *Bio/Technology*, 5, 263-266 |
| Walnut | McGranahan, G. et al. (1990) *Plant Cell Rep.* 8: 512-516 |
| Spruce/Conifer | Ellis, D. et al. (1989) *Plant Cell Rep.* 8: 16-20 |
| Poplar | Pythoud, F. et al. (1987) *Bio/Technology* 5, 1323 |
| Apple | James, D. et al. (1989) *Plant Cell Rep.* 7: 658-661 |

Other *Agrobacterium* strains such as *A. rhizogenes* may be more suitable in some applications. *A. rhizogenes*, which incites root hair formation in many dicotyledonous plant species, carries a large extra-chromosomal element called an Ri (root-including) plasmid, which functions in a manner analogous to the Ti plasmid of *A. tumefaciens*. Transformation using *A. rhizogenes* has developed analogously to that of *A. tumefaciens* and has been used successfully, e.g., to transform alfalfa (73).

Methods of inoculation of the plant tissue vary depending upon the plant species and the *Agrobacterium* delivery system. A convenient approach is the leaf disc procedure which can be performed with any tissue explant that provides a good source for initiation of whole plant differentiation. The addition of nurse tissue may be desirable under certain conditions. Other procedures such as in vitro transformation of regenerating protoplasts with *A. tumefaciens* may be followed to obtain transformed plant cells as well.

Several so-called "direct" gene transfer procedures have been developed to transform plants and plant tissues without the use of an *Agrobacterium* intermediate. Plant regeneration from protoplasts is a particularly useful technique (74). In the direct transformation of protoplasts the uptake of exogenous genetic material into a protoplast may be enhanced by use of a chemical agent or electric field. The exogenous material can then be integrated into the nuclear genome. Early work has been conducted in the dicot *Nicotiana tabacum* (tobacco) where it was shown that the foreign DNA was incorporated and transmitted to progeny plants (75, 76). Monocot protoplasts have typically been transformed by this procedure due to the recalcitrance of monocots to *A. tumefaciens* transformation. For example, Italian ryegrass (76); maize (77); and Black Mexican sweet corn (78) have been successfully transformed. Techniques for transforming a wide range of monocots have been recently reviewed (79, 80).

The direct introduction of nucleic acid into protoplasts of a plant can be effected by treatment of the protoplasts with an electric pulse in the presence of the appropriate nucleic acid using electroporation. In this method, the protoplasts are isolated and suspended in a mannitol solution. Supercoiled or circular plasmid nucleic acid is added. The solution is mixed and subjected to a pulse of about 400 V/cm at room temperature for less than 10 to 100 microseconds. A reversible physical breakdown of the membrane occurs to permit DNA uptake into the protoplasts.

Additionally, DNA viruses have been used as gene vectors in plants. A cauliflower mosaic virus carrying a modified bacterial methotrexate-resistance gene has been used to infect a plant. The foreign gene systematically spreads throughout the plant (81). The advantages of this system are the ease of infection, systemic spread within the plant, and multiple copies of the gene per cell.

Liposome fusion is also an effective method for transformation of plant cells. In this method, protoplasts are brought together with liposomes carrying the desired gene. As membranes merge, the foreign gene is transferred to the protoplasts (82). Similarly, polyethylene glycol (PEG) mediated transformation has been carried out in *N. tabacum* (a dicot) and *Lolium multiflorum* (a monocot). Direct gene transfer is effected by the synergistic interaction between $Mg^{2+}$, PEG, and possibly $Ca^{2+}$ (83). Alternatively, exogenous DNA can be introduced into cells or protoplasts by microinjection in which a solution of plasmid DNA is injected directly into the cell with a finely pulled glass needle.

A recently developed procedure for direct gene transfer involves bombardment of cells by microprojectiles carrying the nucleic acid construct of interest (84, 85). In this procedure, chemically inert metal particles, such as tungsten or gold, are coated with the exogenous DNA and accelerated toward the target cells. At least transient expression has been achieved in onion. Stably transformed cultures of maize and tobacco have been obtained by microprojectile bombardment. Stably transformed soybean plants have also been obtained by this procedure (86).

The invention thus includes plants, seeds, and plant tissue capable of expressing a nucleotide sequence encoding an RSV-containing protein or peptide and, optionally, another substance useful for the stimulation of an immune response in a mammal.

The present invention also relates to an antigenic composition or immunogenic complex comprising a genetically transformed plant tissue and an antigenic agent where the tissue comprises or expresses a nucleotide sequence encoding one or more immunogenic agents. The tissue is capable of inducing an immune response to the expressed immunogenic agent in mammals sufficient to immunize the mammals against the agents when the mammals are administered the plant material, e.g., by oral ingestion. Such a composition is capable of eliciting antibodies in a mammal that are cross-reactive with RSV.

The present invention thus relates to an antigenic composition or immunogenic complex comprising at least a portion of a transgenic plant material. The antigenic composition or immunogenic complex can be in the form of an extract, juice, liquid, powder or tablet. The antigenic composition or immunogenic complex can further comprise a second substance that acts as an adjuvant.

Also contemplated is a method of immunizing a mammal or other animal against RSV by administering an immunologically effective amount of an antigenic composition or immunologic complex of the invention to the mammal. This regimen may further comprise administering a subsequent amount of antigenic composition to the mammal as a booster. Preferably, at least one of these immunizations is performed orally to ensure inducing a mucosal immune response as well as to take advantage of cost and convenience. Conveniently, an oral administration step entails consuming a transgenic plant or plant part of the invention.

A method of producing an aforementioned transgenic plant is also contemplated. The plant is capable of expressing a protein or peptide that is effective in eliciting antibodies cross-reactive with RSV. The method comprises transforming a plant cell with an aforementioned nucleic acid construct and regenerating the transformed plant. Further steps can include cultivating and/or harvesting the plant or a part thereof. Preferred plants for transformation in this regard include tobacco, banana, tomato, potato and carrot.

The present invention also relates to an immunologic or vaccination regimen comprising administering a sufficient oral dose of an antigenic composition or immunogenic complex comprising a transgenic plant-derived material expressing a nucleotide sequence encoding RSV where the system is capable of inducing an immune response to RSV in the mammal sufficient to immunize the mammal against RSV.

The present invention also relates to a method for producing a vaccine or vaccine adjuvant. Such a method comprises constructing a plasmid vector or a nucleic acid fragment by operably linking a nucleic acid sequence encoding RSV, where the material is capable of inducing an immune response in mammals sufficient to immunize the mammals against RSV, with a plant-functional promoter capable of regulating expression of RSV in a plant. A plant cell is then transformed with the vector or nucleic acid fragment to produce a transgenic plant, the plant is grown, and an effective dose is orally administered. The proportion of immunogen and adjuvant can be varied over a broad range so long as both are present in effective amounts. For example, U.S. Pat. No. 5,723,130 discloses effective amounts for adjuvants such as alum (100 µl solution containing 1 µg antibody adjuvanted with 1 µg/ml alum).

The dosages of the compositions (drugs) used in the present invention must, in the final analysis, be set by the physician in charge of the case, using knowledge of the drugs, the properties of the drugs in combination as determined in clinical trials, and the characteristics of the patient, including diseases other than that for which the physician is treating the patient.

Compositions of the invention also may have therapeutic effects and therefore may be administered as a single pharmaceutical composition. Adjunctive pharmaceutical compositions containing an effective amount of a composition in accordance with the invention and a second compound or composition having an adjuvant effect may be administered.

The amounts of each drug to be contained in each dosage unit depends on the identity of the drugs chosen for the therapy, and other factors such as the indication for which the adjunctive therapy is being given. For example, 1 pc (picogram) to 10 mg (milligrams)/kg (kilogram) body weight per vaccine dosage unit, and preferably 1 ng (nanogram) to 100 μg (microgram)/kg body weight, may be used. Such administration of the second component may be provided by means known to pharmaceutical scientists. For example, the total dosage of a second component may be formulated in a manner which provides a substantially constant flow of compound to the patient. At least the following references teach sustained release formulations: German Patent 3632201, capsules; Swiss Patent 634990, tablets; German Patent 2732335, tablets; U.S. Pat. No. 5,260,066, cryogels; European Patent Publication 361894, liposomes.

Pharmaceutical scientists are acquainted in modem practice with the manners of adjusting a sustained release formulation to provide the desired rate of administration of a given compound and such formulations can be prepared by the skill of the pharmaceutical art of the compounds used herein. Such formulations may be combined in a single dosage form with the chosen first component compound. For example, a small tablet or pellets of a second component, formulated to provide constant availability of the compound, may be combined, for example in a capsule, with the first component compound. Still further, a suspension may be prepared in which the first component is present as particles of pure compound, and the particles of the second component are coated to provide sustained release in the body. In such manner, the availability of the second component may be adjusted to provide the desired substantially constant blood levels and, hence, substantially constant potentiation of the first component.

The inert ingredients and manner of formulation of the adjunctive pharmaceutical compositions are conventional, except for the presence of the combination of the first component and the second component compound. The usual methods of formulation used in pharmaceutical science may be used here. All of the usual types of compositions may be used, including tablets, chewable tablets, capsules, and solutions. In general, compositions contain from about 0.5% to about 50% of the compounds in total, depending on the desired doses and the type of composition to be used. The amount of the compounds, however, is best defined as the effective amount, that is, the amount of each compound which provides the desired dose to the patient in need of such treatment. The activity of the adjunctive combinations does not depend on the nature of the composition, so the compositions are chosen and formulated solely for convenience and economy. Any of the combinations may be formulated in any desired form of composition.

Capsules are prepared by mixing the compound with a suitable diluent and filling the proper amount of the mixture in capsules. The usual diluents include inert powdered substances such as starch of many different kinds, powdered cellulose, especially crystalline and microcrystalline cellulose, sugars such as fructose, mannitol and sucrose, grain flours and similar powders.

Tablets are prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant is necessary in a tablet formulation to prevent the tablet and punches from sticking in the die. The lubricant is chosen from such slippery solids as talc, magnesium and calcium stearate, stearic acid and hydrogenated vegetable oils. Tablet disintegrators are substances which swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethylcellulose, for example, may be used, as well as sodium lauryl sulfate.

Enteric formulations are often used to protect an active ingredient from the strongly acid contents of the stomach. Such formulations are created by coating a solid dosage form with a film of a polymer which is insoluble in acid environments, and soluble in basic environments. Exemplary films are cellulose acetate phthalate, polyvinyl acetate phthalate, hydroxypropyl methylcellulose phthalate and hydroxypropyl methylcellulose acetate succinate.

The present inventors have developed novel chimeric nucleic acid constructs that result in higher than previously attainable levels of expression of RSV protein in plant cells. As discussed in Example 2 below, these chimeric nucleic acid constructs can be used to transform plant cells and plants to express antigen of RSV sufficient to induce a protective immune response. A method for preparing the constructs is described in Example 1 below.

Animal Models

Although mice are used in the Examples below, the invention is not limited to the treatment of mice. In addition to mice (101-121), animal models for RSV have been developed in primates (101) (adult rhesus monkeys (129), African green monkeys (130) and bonnet monkeys (135)), calves (101), cotton rats (101, 124-128), guinea pigs (101, 131-133), ferrets (101, 134) and hamsters (101). The use of animal models will permit testing of the efficacy and safety of prophylactic and therapeutic strategies using the plant-derived vaccines of the invention. The development of multiple animal models coincides with the realization that RSV disease in humans is a multifaceted disease whose clinical manifestations and sequelae depend upon age, genetic makeup, immunologic status and concurrent disease with subpopulations. Any one of these models can be employed to test the plant-derived RSV vaccine of the invention.

Using animal models, a complete immunological evaluation, which includes the measuring of systemic and mucosal humoral and cellular immune responses and the measuring of RSV infection in the animal, for example, by determining viral titer in lung by immunoplaque assay by determining serum titers by ELISA, and by assessing bronchiolar inflammation on coded lung sections, (131), can be conducted. For example, antibody in the range of 1 pg to 10 mg/kg body weight, and preferably 1 ng to 100 μg/kg body weight, of the plant-derived vaccine of the invention can be administered both prophylactically and therapeutically in the animal models in accordance with the invention (123). This amount should be sufficient to produce neutralizing activity in treated animals (123, 136).

After the intricate mechanisms constituting the immune network are studied in animal models, treatment strategies and vaccination trials using the plant-derived vaccine of the invention can be conducted in infected patients or healthy volunteers.

In addition, although particular constructs containing the RSV-F coding sequence are used in the Examples below, as discussed above, additional constructs containing sequences encoding for RSV protein and peptides other than RSV-F may be used in accordance with the invention. Thus, for example, chimeric nucleic acid constructs containing RSV-G coding sequences encoding RSV-G protein, or antigenic protein or peptides of RSV-G can be introduced into transgenic plant cells and plants as carried out in the Examples below to prepare antigenic compositions and immunogenic complexes capable of eliciting antibodies in an animal that are reactive with RSV.

EXAMPLE 1

The present inventors discovered that RSV nucleic acid could be expressed and produce a protein antigenically related to authentic RSV protein in apple leaf mesophyll protoplasts. In addition, the inventors discovered that RSV nucleic acid expression could be enhanced by including a viral leader and a plant enhancer within the plant transformation vector. Towards this end, chimeric nucleic acid constructs were generated containing a translation enhancer from the 5'-untranslated leader of alfalfa mosaic virus (AMV) (50) and a transcriptional enhancer from the pea PetE promoter (27) fused to the CaMV 35S promoter and the RSV-F gene. Transient expression of these chimeric nucleic acids was analyzed in apple protoplasts by enzyme-linked immunosorbent assay (ELISA) and immunoblotting.

Materials and Methods for Example 1

Generation of chimeric nucleic acid constructs. Chimeric nucleic acid constructs containing the RSV-F coding sequence were generated to assay F-protein expression in apple leaf mesophyllprotoplasts. A 1.75-kbp RSV-F cDNA (26) (gift from Peter Collins, National Institutes of Health, Bethesda, Md.) in pBR322 was amplified by PCR using Pfu DNA polymerase (Boehringer-Mannheim). The oligonucleotide primers used (forward primer 5'-CACGCGGC-CGCTAACAATGGAGTTGCTAATCCTCA-3' (SEQ ID NO:5) carrying a Non site and reverse primer 5'-CAC-GAGCTCTTTATT-TAGTTACTAAATGCAATA-3' (SEQ ID NO:6) carrying an SstI site) were designed to encompass the RSV-F start and stop codons, respectively. The 1.75-kbp amplified fragment was ligated into pBlueScript II KS, opened at NotI and SstI sites to give pJSS2, and its sequence was confirmed by the dideoxynucleotide chain-termination method. The RSV-F fragment, flanked with XbaI and SstI sites, was cleaved from pBlueScript II KS and ligated into the binary plant vector pBI121 (Clontech) by replacing the constituent GUS gene at XbaI and SstI sites, yielding pJSS3 (FIG. 1).

To produce a promoters negative control, the CAM 35S promoter driving the expression of the RSV-F gene in pJSS3 (FIG. 1) was removed by HindIII and XbaI digestion. The ends of the plasmids were then made flush using Klenow polymerase (Gibco-BRL) and religated by T4 DNA polymerase (Gibco-BRL) to generate pJSS5 (FIG. 1).

The 37-bp 5'-untranslated leader sequence from the AMV RNA4 gene (50) was added to the RSV-F gene by PCR using a forward primer encompassing the 37-bp AMV leader and 27 bp from the RSV-F start codon in pJSS2 (5'-CACTCTA-GAGTTTTTATTTT-TAATTTTCTTTCAAATACTTCCATCATGGAGTGC TAATCCTCAAAGCAAAT-3' (SEQ ID NO:7) carrying an XbaI site) and the same reverse primer as above. The 1.79-kbp amplified fragment was ligated into pBlueScript II KS at XbaI and SstI sites and its sequence confirmed. The fragment was used to replace the RSV-F sequence at XbaI and SstI sites in pJSS3 to generate pJSS11 (FIG. 1).

A 268-bp enhancer (P268) from the pea plastocyanin gene promoter (27) (gift from Advanced Technologies, Cambridge, UK) was ligated into HindIII-cut and dephosphorylated pJSS11 (FIG. 1). The enhancer, flanked with HindIII sites, was inserted in pJSS11 in reverse orientation to generate pJSS14 (FIG. 1).

The reporter constructs (FIG. 1) were used to transform a methylation-deficient *E. coli* strain, JM110, to avoid suppression of expression in plant cells caused by the methylation of CpG bases (51). Greatly enhanced expression of RSV-F can be obtained by producing plant synthetic genes with optimized codon usage similar to that carried out in other systems (57, 58, 90). The plasmid DNAs were prepared for transfection assays using Qiagen midi columns (Qiagen, Santa Clara, Calif.).

Preparation and Transfection of Apple Leaf Mesophyll Protoplasts. Leaves from 3-week-old tissue-culture-grown *Malta x domestica* cv. Gala shoots were used to isolate protoplasts according to the method of Wallin and Johansson (52). Protoplasts were counted with a hemacytometer and diluted to a concentration of $0.5 \times 10^6$ protoplasts/ml. Transfections were carried out on the same day using a single preparation of protoplasts. Protoplasts in aliquots of 60 μl were transfected with 10 μg chimeric nucleic acid construct DNA using PEG as described by Wilde et al. (53). The transfections with individual chimeric gene constructs and the TE buffer (10 mM Tris-HCl pH 7.4, 1 mM EDTA pH 8.0) control were replicated ten times. After 24 h, protoplasts were split into two batches and pelleted by centrifugation in 1.5-ml microfuge tubes at 1600 g for 5 min in an Eppendorf 5417 bench-top centrifuge. One batch was used for ELISA and the other for protein extraction.

Analysis of RSV-F Protein by ELISA.

Protoplasts from each replicate were suspended in 100 μl coating buffer where they lysed in 2-3 min and were then used to coat ELISA microtiter plate wells (Immulon 1B, Dynex Technologies) and analyzed as described by Clark and Adams (33). The primary monoclonal antibody against the RSV-F protein (Serotec) was diluted 1:1000, and 50 μl was added to each well. Secondary antibody, alkaline phosphatase-conjugated rabbit anti-mouse IgG (Sigma), was diluted 1:1000 and 50 μl was added to each well. The presence of label was detected by adding 50 μl of nitrophenyl phosphate to each well, and ELISA readings were recorded at 405 nm in a microplate autoreader (MRX, Dynex Technologies). To determine whether the amount of RSV-F accumulated in protoplasts with each construct differed significantly, the mean ELISA values for each construct were compared using t-tests.

Protein Extraction, SDS-PAGE, Electroblotting, and Immunoblot Assay.

Proteins were extracted from transfected apple leaf mesophyllprotoplasts as described by Wang et al. (54) and mixed with an equal volume of SDS-PAGE loading buffer (55). The mixture was boiled at 95° C. for 5 min. Gels were electrophoresed at 100 V for 2-3 h until the dye front was about 5 mm from the bottom of the gel. Resolving gels were polymerized at 15% (wt/vol) acrylamide and stacking gels at 5% (wt/vol) acrylamide. Separated proteins were transferred to a 0.45-μm nitrocellulose membrane using a semi-dry transfer apparatus according to the manufacturer's instructions (BioRad). Transferred proteins were subjected to primary labeling with a 1:1000 dilution of monoclonal antibodies against RSV-F (Serotec), followed by secondary labeling with a 1:3000 dilution of goat anti-rabbit IgG alkaline phosphatase conjugate. The label was analyzed using an Immun-Blot assay kit (BioRad) according to the manufacturer's instructions.

Results and Discussion for Example 1

A series of chimeric nucleic acid constructs were generated by fusing an AMV RNA4 leader and an enhancer (P268) to the CaMV 35S promoter driving the expression of the RSV-F gene (FIG. 1). The recombinant RSV-F gene expression was analyzed by ELISA following PEG-mediated transfection of apple leaf mesophyllprotoplasts.

A trace amount of non-specific antibody binding was observed in protoplasts transfected with the TE buffer in the absence of DNA. To analyze the results, the absorbance in protoplasts transfected with chimeric gene constructs was compared to that of the promoterless control (pJSS5) after subtracting the absorbance of the protoplasts transfected with the TE buffer. Protoplasts transfected with the promoterless RSV-F construct (pJSS5) produced a low level of RSV-F antigen ($A_{405\ nm}$=0.002±0.001) (FIG. 2).

Figure 2:
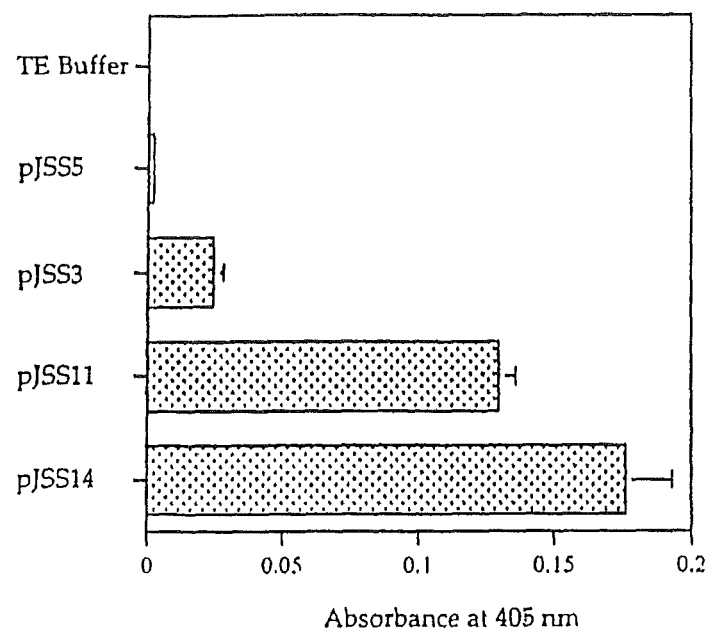
FIG. 2 shows expression of RSV-F chimeric nucleic acid constructs (FIG. 1) transfected into apple leaf protoplasts. Measurements were done by ELISA with the absorbance recorded at 405 nm 30 min after incubation with the substrate. A total of ten replicates per construct and TE buffer (negative control) were analyzed. Bars correspond to means±SE.

The mean $A_{405\ nm}$ value from protoplasts transfected with the plasmid containing the RSV-F gene inserted downstream of the CaMV 35S promoter (pJSS3) was 12-fold higher than that from the promoterless control (pJSS5) (FIG. 2). This indicates that the RSV-F gene driven by the CaMV 35S promoter can express a protein antigenically related to authentic F-protein in transfected apple protoplasts.

The CaMV 35S promoter has been shown to contain multiple domains that function either independently or synergistically in a developmentally and tissue-specific manner to facilitate expression in various cell types (37). In an attempt to increase RSV-F expression, a 37-bp AMV RNA4 untranslated leader sequence was fused between the CaMV 35S promoter and the RSV-F gene in plasmid pJSS11 (FIG. 1). The mean amount of RSV-F antigen synthesized from pJSS11 was significantly ($P \le 0.01$) higher (5.5-fold) compared to pJSS3 which contains the RSV-F gene driven by the CaMV 35S promoter without the leader (FIG. 2). To test if RSV-F gene expression could be increased further, the P268 enhancer was fused upstream of the CaMV 35S promoter in pJSS11 to obtain pJSS14 (FIG. 1). As a result, RSV-F expression was significantly enhanced 7.3-fold higher than pJSS3 ($P \le 0.01$) and 1.4-fold higher than pJSS11 ($P \le 0.05$) (FIG. 2). This showed that combining transcriptional and translational enhancers with the CaMV 35S promoter can increase several-fold the expression of a recombinant human viral gene in plant cells.

Figure 3:
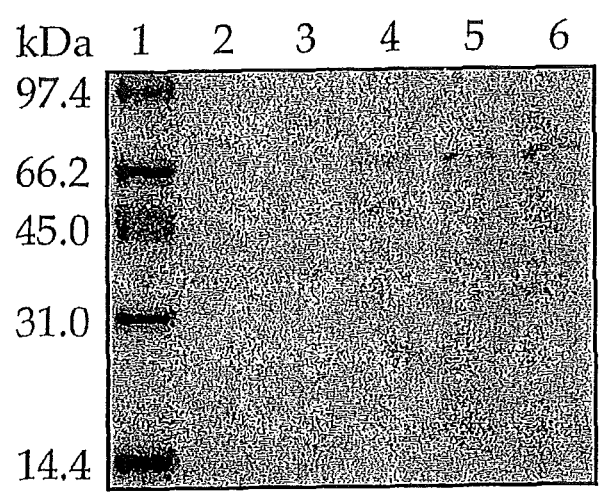
FIG. 3 shows immunoblot analysis of proteins extracted from transfected apple protoplasts: lane 1: protein molecular weight marker, lane 2: proteins extracted from protoplasts transfected with TE buffer in the absence of DNA, lanes 3, 4, 5, 6: proteins extracted from protoplasts transfected with the pJSS5, pJSS3, pJSS11, and pJSS14 RSV-F nucleic acid constructs (FIG. 1), respectively.

The ELISA results (FIG. 2) were confirmed by immunoblotting proteins isolated from protoplasts. Blotted proteins were detected by antibody binding with monoclonal antibodies against RSV-F. Antigenic cross-reactivity was observed at a molecular mass of 68-70 kDa (FIG. 3), which represented the RSV-F fusion protein (56). This demonstrated expression of a protein of the expected molecular mass and antigenicity in apple protoplasts.

The RSV-F gene can be expressed in plant cells. Further, the expressed RSV-F protein is recognized specifically by the monoclonal antibodies raised against authentic F-protein. In addition, the accumulation of the recombinant protein can be enhanced by modifying the transfection vector with the addition of enhancer and leader sequences. A stable transformation system for apple using *Agrobacterium*-mediated transfer is available (De Bondt et al. 1996). Overall, these results with transient assays suggest that modification(s) in a plant transformation vector will help achieve the high titer of viral antigen in transformed plants required for them to be useful as vaccines.

The present inventors discovered that introducing chimeric gene constructs containing the RSV-F coding sequence into genetically engineered tomato could serve as a novel delivery system for oral immunization of BALB/c mice. The immunized mice produced both serum and mucosal antibodies against the RSV-F antigen. A method for preparing the oral delivery vaccine and the use thereof is described in Example 2 below.

EXAMPLE 2

Materials and Methods for Example 2

Chimeric gene constructs. Plasmids containing the RSV-F coding sequence downstream of the constitutively expressed cauliflower mosaic virus (CaMV) 35S promoter and the preferentially fruit-expressed E8 promoter were constructed as follows. A 1.75 kbp-DNA fragment representing the RSV-F coding region (26) (gift from Dr. P Collins, National Institutes of Health, Bethesda, Md.) was amplified by the polymerase chain reaction (PCR) using Pfit DNA polymerase (Boehringer-Mannheim Indianapolis, Ind.). The forward and reverse primers were designed to complement the RSV-F start initiation and termination codons, respectively (27). The 1.75 kbp-amplified fragment was ligated into pBlueScript II KS (Stratagene, La Jolla, Calif.) opened at NotI and SstI sites, and its sequence was confirmed. The RSV-F fragment was cleaved from pBlueScript II KS with XbaI and SstI and ligated into the binary plant vector pBI121 (Clontech, Palo Alto, Calif.) where it replaced the constituent GUS gene and yielded pJSS3 (FIG. 1). The 2.2 kbp E8 promoter from tomato (28) (gift from Dr. C. Voelker, University of California, Berkeley) was cleaved from the pUC118 plasmid with EcoRI and BamIII and ligated into pBlueScript II KS opened at these restriction sites. This provided a HindIII site at the 5'-end of the E8 promoter. The CaMV 35S promoter upstream of the RSV-F gene in pJSS3 (FIG. 1) was removed by HindIII and BamI digestion and replaced by the E8 promoter to give pJSS4 (FIG. 1).

Tomato Transformation.

Plasmids pJSS3 and pJSS4 were mobilized into *Agrobacterium tumefaciens* strain GV3101 (pMP90) (29) (gift from Dr. S. Gelvin, Purdue University, Ind.) via electroporation and used to transform cherry tomato (*Lycopersicon esculenrum* Mill. Cv. Swifty Belle) following modification of protocols described by Bird et al. (30) and Hamza and Chupeau (31). Eight-day-old cotyledons were excised from in vitro-germinated seedlings, and cocultivated for 48 hr with an overnight-grown culture of *A. tumefaciens* carrying the plasmids on a cocultivation medium consisting of Murashige and Skoog (MS) salts, Gamborg's B5 vitamins, supplemented with 1 mg/l α-naphthaleneacetic acid, 1 mg/l thidiazuron (TDZ), 640 mg/l 2-[N-morpholino]ethane sulfonic acid, 30 g/l sucrose, and 6.5 g/l Difco-bacto agar. The pH of the medium was adjusted to 6.1 with 1N NaOH. Cotyledons were then rinsed with sterilized deionized water, blotted dry on a sterilized paper towel, and placed onto a selection medium consisting of MS salts and Gamborg's B5 vitamins, and supplemented with 0.5 mg/l 6-benzyladenine, 1 mg/l TDZ, 0.5 mg/l 3-indoleacetic-acid, 100 mg/l kanamycin, 500 mg/l carbenicillin, and 6.5 g/l Difco bacto-agar. The pH was adjusted to 5.8 with 1 N NaOH. After six weeks, kanamycin-resistant shoot regenerants were removed from callus, and transferred to a rooting medium consisting of MS salts with Gamborg's B5 vitamins, 30 g/l sucrose, and 6.5 g/l Difcobacto agar (pH was adjusted to 5.8). Rooted plantlets were acclimatized and transferred to a greenhouse for fruiting. Transgenic plants were confirmed for the presence of transgene(s) in leaf tissue using Southern blot analysis (32).

Analysis of Transformed Tomato Plants for RSV-F Protein.

Tomato plant tissue was homogenized with a mortar and pestle in 3 volumes of coating buffer (33) to extract total protein. One hundred μl of the homogenate was used to coat each well of an enzyme-linked immunosorbent assay (ELISA) microtiter plate (Immulon 1B, Dynex Technologies, Chantilly, Va.) and analyzed as described by Clark and Adams (33). Monoclonal antibody against the RSV-F protein (Serotec, Raleigh, N.C.) was diluted 1:1000, and 50 μl were added to each well. Secondary labelling was done using an alkaline phosphatase-conjugated rabbit anti-mouse IgG (Sigma, St. Louis, Mo.) at a 1:1000 dilution with 50 μl added to each well. The label was detected by adding 50 μl of nitrophenyl phosphate to each well, and ELISA readings were recorded at 405 nm in a microplate autoreader (MRX, Dynex Technologies). A standard curve using purified RSV was plotted to estimate the amount of recombinant protein expressed in transgenic plant tissue. Total soluble protein in the plant samplers was measured according to Bradford (34).

Protein Extraction, Gel Electrophoresis, Electroblotting, and Immunoblot Assay.

Proteins were extracted from leaf, stem, root and fruit tissue of tomato plant 120, precipitated using acetone and resuspended in extraction buffer as described by Mason et al. (35). An equal volume of SDS-PAGE loading buffer was added to each 25 μl (25 μg) protein sample. The mixture was heated at 95° C. for 5 min and separated on SDS-polyacrylamide gels consisting of stacking gels of 5% (w/v) acrylamide and resolving gels of 15% (w/v) (32). Gels were electrophoresed at 100 V for 2-3 h until the dye front was about 5 mm from the bottom of the gel. Proteins were electrophoretically transferred to 0.45 μm nitrocellulose membranes for 15 min at 30 V using a semi-dry transfer apparatus (BioRad, Hercules, Calif.) according to the manufacturer's instructions. Transferred proteins were subjected to primary labeling with a 1:1000 dilution of monoclonal antibodies against RSV-F (Serotec), followed by secondary labeling with a 1:3000 dilution of goat anti-rabbit IgG alkaline phosphatase conjugate (BioRad). The label was analyzed using an Immun-Blot assay kit (BioRad) according to the manufacturer's instructions. Oral immunization with RSV-F. Twenty five female BALB/c mice were fed tomato plant (fruit) tissue containing approximately 32.5 μg RSV-F/g total soluble protein. Five control mice were fed wild-type cherry tomato. A total of five feedings were done on days 0, 4, 14, 18 and 28 essentially as described by Haq et al. (14).

Antibody Assays.

Animals were bled on day 32 as described by Haq et al. (14) and sera were stored at −20° C. until assayed. On day 33, the mice were given a single intramuscular injection (50 μl) of "RSV antigen" gamma-ray killed RSV in a cellular extract (Biodesign International, Kennebunk, Me.) in phosphate buffered saline at 12 mg/ml. All the mice were euthanized on day 39 and their sera assayed for RSV antigen. The small intestine from the duodenum to the ileal-cecal junction was excised to determine the presence of mucosal IgA antibodies secreted in response to RSV-F ingestion. Mucosal extracts were prepared essentially according to Clements et al. (36). Antibody titers were analyzed by ELISA for production of antibodies to RSV. The serum and mucosal samples drawn from the preimmunized, immunized and mice boosted with RSV were analyzed by endpoint titer dilutions, and 50 μl were added to each well of an ELISA microtiter plate coated with 12 μg/ml of RSV antigen in coating buffer (33). Secondary labeling was done using alkaline phosphatase-conjugated rabbit-antibodies specific for mouse IgG, IgA, (Sigma), $IgG_1$, $IgG_{2a}$ or $IgG_{2b}$ (Zymed, South San Francisco, Calif.) at a 1:1000 dilution. Labeling was detected with nitrophenyl phosphate and the absorbance was quantitated at 405 nm (33). Individual samples were replicated 3 times to confirm the reliability of the results. Absorbance was calculated after subtraction of background values obtained in wells coated with buffer. Antibody titers were calculated by comparing absorbance values of serially-diluted serum of control and immunized mice. The endpoint titers were those dilutions at which the mean absorbance readings obtained from control and immunized mice were not significantly different.

Results and Discussion for Example 2

Generation of Transgenic Tomato Plants Producing RSV-F Antigen.

Figure 4:
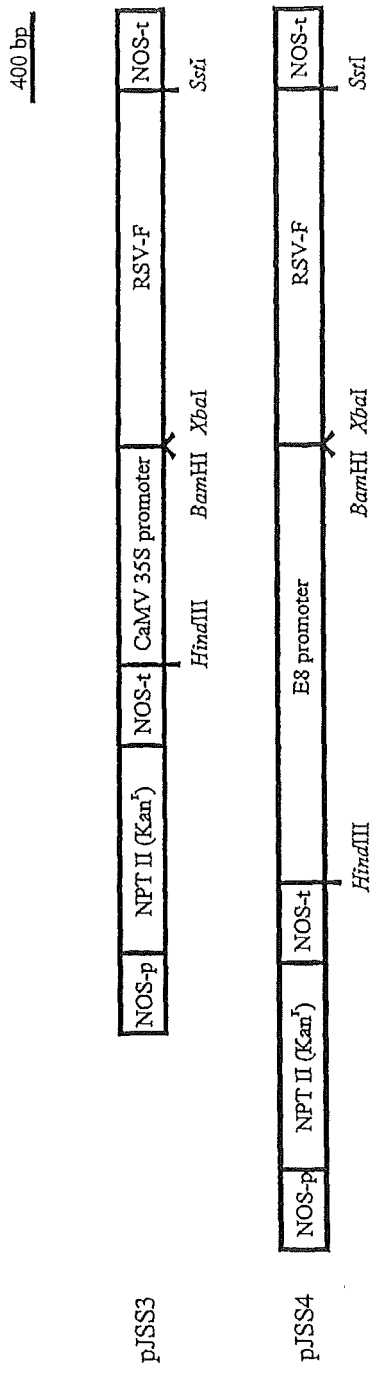
FIG. 4 shows the RSV-F nucleotide-coding-sequence under the transcriptional control of either the CaMV 35S or E8 promoter inserted into plasmids. Restriction enzyme sites used for making the constructs are indicated. Plasmids are designated on the left. NOS-p: nopaline synthase promoter; NOS-t: nopaline synthase terminator.
Figure 5:
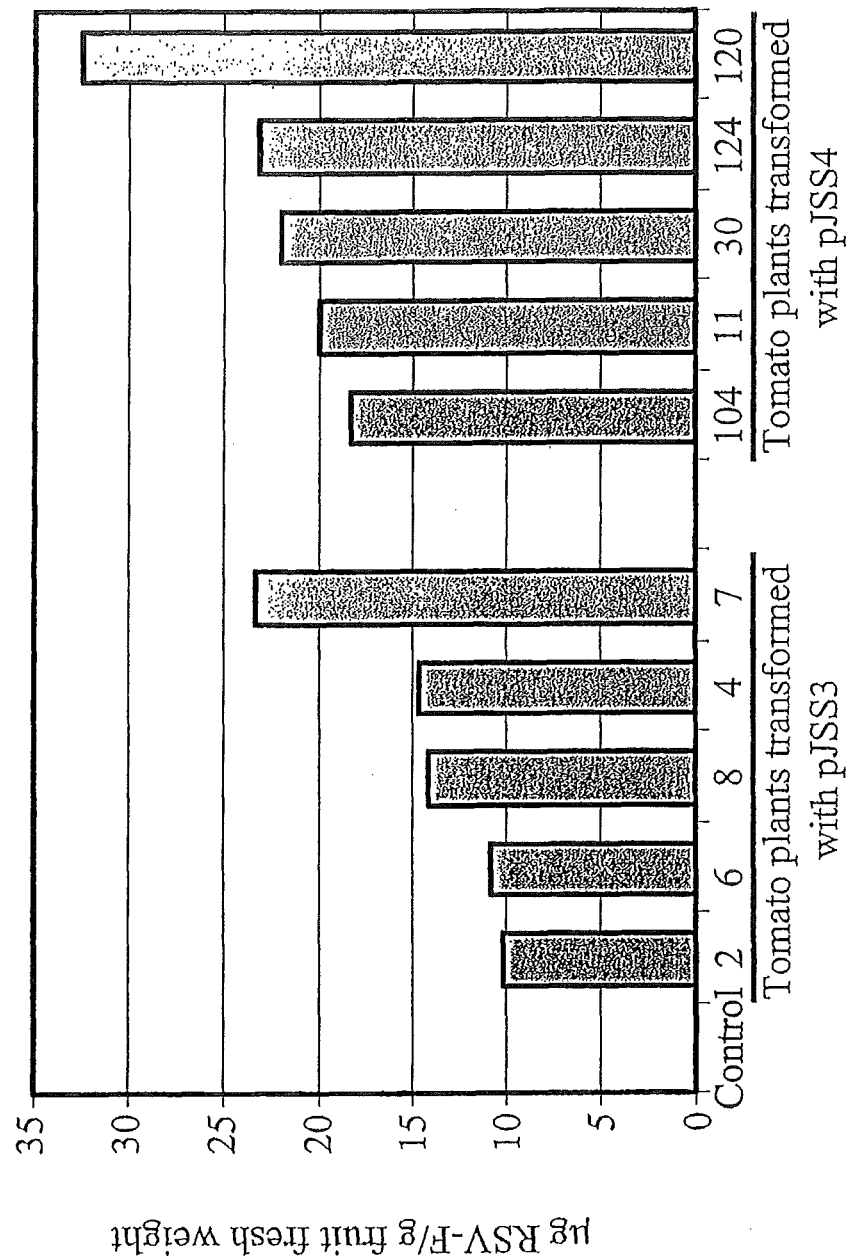
FIG. 5 shows the amount of recombinant RSV-F antigen in transgenic tomato plants transformed with the pJSS3 and pJSS4 constructs (FIG. 4). For each construct, five transgenic plants expressing the highest levels of RSV-F antigen are shown. Wild-type tomato was used as a control. The numbers on the bottom of the figure represent different tomato lines.
Figure 6:
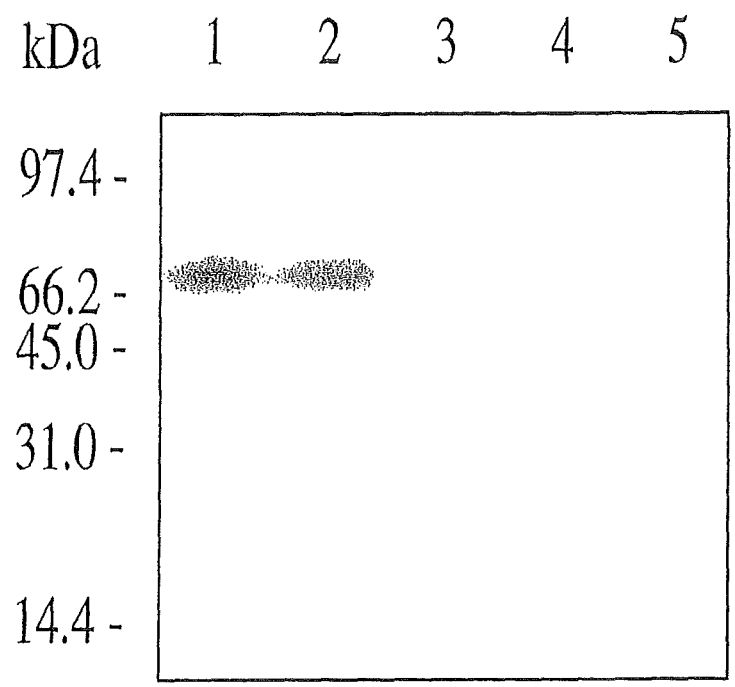
FIG. 6 shows immunoblot analysis of proteins extracted from transgenic tomato line 120 transformed with the pJSS4 construct. Lane 1: RSV antigen; Lane 2: proteins extracted from fruit tissue; Lanes 3, 4, and 5: proteins extracted from leaf, stem and root tissues, respectively.
Figure 7A:
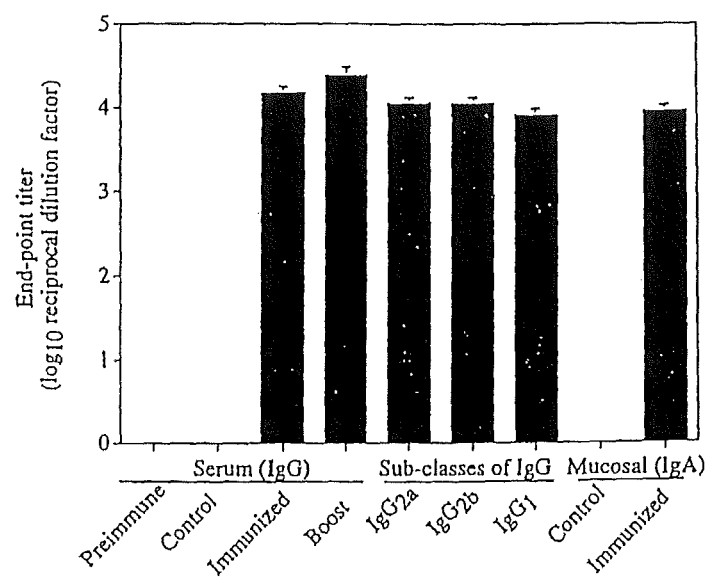
FIG. 7A shows serum and mucosal RSV-F specific antibody titers from mice fed transgenic and control tomatoes. Sera were collected prior to feeding and, on day 32, from control (mice fed wild-*type tomato) and immunized mice (fed transgenic tomatoes) to determine RSV-F-specific IgG titers. On day 39, sera samples were collected from the same mice after intramuscular injection (boost) with inactivated RSV and analyzed to determine the effect of the boost on IgG titers and the relative amounts of three classes ($IgG_{2a}$, $IgG_{2b}$ and $IgG_1$) of RSV-F specific IgG titers. On day 39, intestine samples also were collected from the same mice and analyzed to determine RSV-F specific IgA titers. Samples were serially diluted and read in triplicate by ELISA. End point titer are plotted (mean±SE) as login of the reciprocal of the dilution factor.
Figure 12:
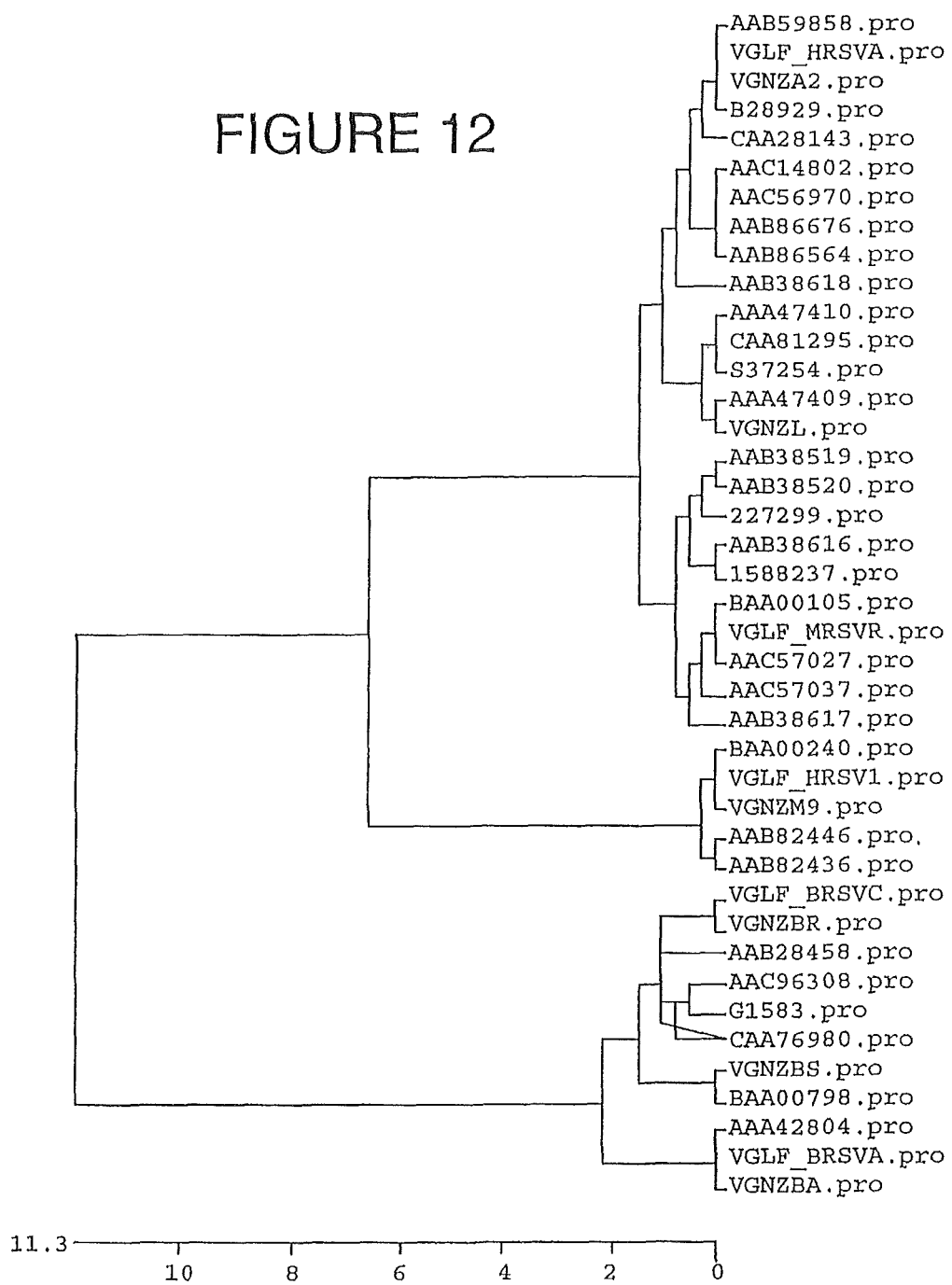
FIG. 12 shows a phylogenetic tree of 41 full-length F protein sequences from the Genbank database. The sequences were aligned using the Clustal V algorithm (Higgins, D. G. & Sharp, P. M.; 1989. Fast and sensitive multiple sequences alignments on a microcomputer. *CABIOS* 5 no. 2: 151-153) via the DNASTAR analysis software, applying the default values. This algorithm produces a value for similarity based upon both absolute amino-acid sequence conservation and evolutionary conservation using the PAM250 weighting table. The X-axis is in units of substitution events. Protein sequence names refer to the Genbank accession numbers. The following sequences are BRSV F proteins: VGLF_BRSVC, VGNZBR, AAB28458, AAC96308, JQ1583, CAA76980, VGNZBS, BAA00798, AAA42804, VGLF_BRSVA, VGNZBA.

The human RSV gene encoding the F protein was placed under the transcriptional control of either the constitutively expressed CaMV 35S promoter (37) or the fruit specific E8 promoter (38) to make chimeric gene constructs pJSS3 and pJSS4 (FIG. 4). Through *Agrobacterium*-mediated transformation, 30 independent transgenic tomato plants were generated with each construct and confirmed by Southern blotting (data not shown). ELISA analysis demonstrated that recombinant RSV-F antigen was expressed in the tomato plant cells. Sixteen transgenic plants containing pJSS3 and 19 containing pJSS4 expressed the RSV-F antigen at levels ranging from 1.0 to 32.5 μg/g of fruit fresh weight. The amount of RSV-F in the plant tissue varied among different transgenic lines; however, the average level in transgenic plants containing the E8 and CaMV 35S promoters was similar, 12.68±2.55 and 9.01±1.87 μg/g fruit fresh weight, respectively. The transgenic plant designated as line 120 (FIG. 5) accumulated the highest amount of RSV-F protein (32.5 μg/g of fruit fresh weight). Immunoblot analysis of proteins extracted from leaf, stem, root, and fruit tissues of tomato plant 120 using monoclonal antibodies specific for RSV-F showed antigenic cross-reactivity in fruit extracts with a 68-70 kDa protein that comigrated with RSV antigen (FIG. 6). No cross-reacting bands were observed in leaf, stem, or root extracts (FIG. 6). This demonstrated the tissue (or fruit) specific expression of the 68-70 kDa RSV-F protein gene under the control of the E8 promoter. Thus, expression of a protein of the expected molecular mass and antigenicity in the tomato plants suggested their possible use as vaccines.

Induction of Both Serum and Mucosal Antibodies and an Immune Response Against RSV.

Tomato fruit from line 120 was orally fed to 25 mice at five times during a 28-day period to test the ability of the expressed RSV-F protein to prime mucosal and serum response. For each feeding, each mouse was given 5 to 7 g of tomato fruit containing 162.5 to 227.5 μg recombinant RSV-F protein. Each mouse consumed approximately 3 to 4 g of tomato tissue. RSV-F specific antibody induction was determined using ELISA on serum collected on day 32 from pre-immunized, immunized and control mice (fed wild-type tomato). Among the 25 orally immunized mice, 22 showed significant serum response and produced anti-RSV-F antibodies. FIGS. 7A-7E show the mean serum anti-RSV-F antibody titers in all 25 mice (endpoint titer was 1:15000). The preimmunized and the control mice did not produce detectable anti-RSV-F antibodies (FIGS. 7A-7E). This demonstrated successful oral immunization of mice and showed that plant-derived RSV-F was active as an oral immunogen.

To test their response to an inactivated RSV antigen, mice were boosted with gamma-radiation-inactivated RSV administered parenterally. The antigen did not cause disease symptoms and the mice continued to show good appetites and appeared healthy. The 32 day serum RSV-F antibody titers before the boost were compared with the RSV-F titers from the serum collected on day 39. All 25 animals in the immunized group, including the 3 that had very low serum anti-RSV-F antibodies following oral immunization, showed significant immune response. Six animals showed 3-4 fold increases in antibody titers, and the mean of the end point serum titer in all 25 was 1:24000 (FIGS. 7A-7E). None of the nonimmunized mice developed measurable anti-RSV-F antibodies. This indicated that mice were primed to recognize the F antigen as presented in inactivated RSV particles following oral immunization with the RSV-F subunit expressed in the tomato plant.

To test the mucosal immune response to the transgenic tomato plant, intestinal extracts were tested by ELISA for RSV-F-specific IgA titers. Intestines were collected from both immunized and control mice on day 39. Among the 22 immunized mice with significant serum antibody response, 18 also had significant RSV-F-specific intestinal IgA titers. However, the intestinal IgA titers of all 25 mice (end-point titer was 1:9000) were significantly lower than those for IgG (FIGS. 7A-7E). None of the nonimmunized mice developed IgA specific antibodies (FIGS. 7A-7E). Thus, oral immunization with the transgenic tomato plant elicited an antigen-specific mucosal IgA response.

Th1 and Th2-type immune responses result in the production of characteristic sets of IgG subclasses. Th1-type responses characteristically result in significant levels of $IgG_{2a}$ and $IgG_{2b}$ while Th2-type responses result in $IgG_1$. The relative amounts of the three classes of RSV specific IgGs were determined from the orally immunized mice. $IgG_{2a}$ and $IgG_{2b}$ were found to be present in significantly high titers (endpoint titer was 1:11000) compared to $IgG_1$ (endpoint titer 1:8000) (FIGS. 7A-7E) suggesting that the transgenic plant-derived RSV-F antigen primes a Th1-type response.

RSV-F antigen expressed in transgenic tomato plant has been shown here to produce serum and mucosal immune responses in a murine system suggesting the possibility of producing a vaccine against RSV and perhaps also other mammalian viruses utilizing the present system. The preferentially fruit-expressed E8 promoter that is activated at the onset of ripening in tomato fruit (38, 39) and the constitutively-expressed CaMV 35S promoter (37) were used to drive the RSV-F gene expression. The E8 promoter was at least as effective in ripening fruit as the CaMV 35S promoter (FIG. 5), and transgenic plants containing the E8 promoter produced sufficient antigen to stimulate the production of mucosal and serum antibody responses in mice (FIGS. 7A-7E). This result is consistent with recent studies showing that plant-derived microbial antigens, for example, the binding subunit of *Escherichia coli* heat-labile enterotoxin (LT-B) (14) and the cholera toxin B subunit (16), successfully serve sources of oral delivery vaccines in mice. The feeding of raw transgenic potato tubers expressing the LT-B subunit to human volunteers also resulted in their production of specific antibodies (18), showing that a plant-based vaccine is safe for mammals and animals.

The hypersensitivity to RSV infection associated with some inactivated and subunit vaccines is limited to individuals without prior exposure to RSV (40). After a single dose of a nonreplicating vaccine, antibody titers first rise in response to the antigen and then decline. When these individuals are challenged a second time, their immune systems produce a faster and more potent response. In RSV infections, this second exposure can lead to a Th2-type response that is characterized by the infiltration of infected lung tissues with eosinophils (11). The eosinophils produce compounds meant to slow the spread of invading extracellular pathogens, for example, bacteria, which in turn irritate lung tissues and lead to enhanced disease (11). However, each subsequent exposure to the antigen induces the proliferation of more antigen-specific memory B cells and results in a more persistent and relatively high level of antibody production. Hence, individuals who have received multiple mucosal exposures to RSV antigens would be expected to have relatively high titers of RSV-specific antibodies and show a much less dramatic increase in antibody titer in response to RSV infection than individuals who received a single dose of inactivated vaccine. This is consistent with the results of the RSV boost of the orally immunized mice presented here (FIGS. 7A-7E).

An oral delivery subunit-vaccine against RSV, produced by expressing the RSV-F protein in plant, is a novel delivery system that has not been reported previously. It is well documented that an RSV-F subunit vaccine does not produce a hypersensitive response in children previously infected with RSV (41-43) and in those who have experienced two or more RSV seasons before vaccination (44). Further, another F-subunit vaccine has protected against RSV in the elderly (45) and in children with cystic fibrosis (46) and bronchopulmonary dysplasia (47). Thus, as a vaccine, the RSV-F subunit appears safe and well tolerated in mammals and animals.

The immune response primed by oral delivery of RSV is a viable means of protecting animals against RSV disease. Both the cotton rat and BALB/c mice (as used here) are model systems for studies on RSV-induced pathology and immune responses (40, 48). Mammals and animals can be readily infected with RSV, develop similar lung pathology, recruit eosinophilis to RSV-infected lung tissue after a single immunization with formalin-inactivated RSV, and show a Th1-type response to infection by wild-type RSV. Recently, BALB/c mice have been used extensively to investigate the basis for the vaccine-enhanced disease that has slowed the development of an effective RSV vaccine (40). These mice are an appropriate system in which to characterize the immune responses to and effectiveness of a plant-derived vaccine for RSV.

Experiments have shown that there is some level of cross-protection between bovine and human strains of RSV in vitro (62). Bovine RSV, which is structurally and antigenically similar to human RSV (compare FIGS. 8 and 9, 10 and 11, and 12 and 13, which are nucleotide sequences for human RSV and bovine RSV, F and G, respectively), may also be expressed in plant tissue and used to prepare an oral delivery vaccine in accordance with the invention. The bovine RSV, which has been shown effective in treatment of cows and calves (93), can be used to treat other mammals.

As discussed above, experiments have also shown that homologous sequences and mimotopes of RSV are capable of eliciting an immune response effective against RSV infection. Since RSV can be repeatedly infectious throughout life (1, 4), development of serum immunity does not seem to be very protective against the infection. However, prior RSV infections do reduce the frequency and severity of RSV-induced lower respiratory tract disease (49). Multiple exposures at the mucosa to virus antigens during RSV infections have been hypothesized to "mature" initial Th2-type responses to more protective Th1-type responses (11). It is contemplated in accordance with the invention that protection against RSV infection will be obtained by stimulation of the mucosal system by a plant-derived oral delivery vaccine of the invention (8). In this light, repeated stimulation of the mucosal system by a plant-derived oral delivery antigen administered during the RSV season may provide appropriate protection.

Although the present invention has been fully described by way of examples with reference to the accompanying drawings, it is to be noted that various changes and modifications will be apparent to those skilled in the art. It is therefore intended that the foregoing detailed description be understood that it is the following claims, including all equivalents, which are intended to define the scope of this invention. Therefore, unless such changes and modifications depart from the scope of the present invention, they should be construed as being included therein.

REFERENCES

1. Hall. C. B. (1992) in Textbook of Pediatric Infectious Diseases. eds. Feigen. R. D. & Chemy. J. D. (Saunders, Philadelphia), Vol. II, pp. 1633-1656.
2. McIntosh, K. & Chanock, R. (1990) in Virology, eds. Fields, B., Knipe, D. & et al. (Raven Press, New York), pp. 1045-1072.
3. Prober, C. G. & Wang, E. E. (1997) Pediatrics 99, 472-5.
4. Tristram, D. A. & Welliver, R. C. (1996) Contemp. Pediat. 13, 47-63.
5. Fleming, D. M. & Cross, K. W. (1993) Lancet 342, 1507-10.
6. Falsey, A. R. & Walsh, E. E. (1998) J. Infect. Dis. 177, 463-6.
7. DeVincenzo, J. (1997) Adv. Pediat. Infect. Dis. 13, 1-47.
8. Coffin, S. E. & Offit, P. A. (1997) Adv. Pediat. Infect. Dis. 13, 333-48.
9. Kim H. W., Canchola, J. G., Brandt, C. D., Pyles, G., Chanock, R. M., Jensen, K. & Parron, R. H. (1969) Amer. J. Epidemiol, 89, 422-434.
110. Hall. C. B. (1994) Science 265, 1393-1394.
11. Srikiatkhachom, A. & Braciale, T. J. (1997) J. Exp. Med. 186, 421-432.
12. Braciale, T. J., Morrison, L. A., Sweetser, M. T., Sambrook, J., Gething, M. J. & Braciale, V. L. (1987) Immunol. Rev 98, 95-114.
13. Strobel, S. & Mowat, A. M. (1998) Immunol. Today 19, 173-181.
14. Haq, T. A., Mason, H. S., Clements, J. D. & Arntzen, C. J. (1995) Science 268, 714-6.
15. Mason, H. S., Ball, J. M., Shi. J. J., Jang, X., Estes, M. K. & Arntzen, C. J. (1996) Proc. Natl. Acad. Sci. USA 93, 5335-40.
16. Arakawa, T., Chong, D. K. & Langridge, W. H. (1998) Nature Biotechnology 16, 292-7.
17. Arntzen, C. J. (1997) Nature Biotechnology 15, 221-2.
18. Tacket, C. O., Mason, H. S., Losonsky, G., Clements, J. D., Levine, M. M. & Arntzen, C. J. (1998) Nat. Med. 4, 607-9.
19. Levine, S., Klaiber-Franco, R. & Paradiso. P. R. (1987) Gen. Virol. 68, 2521-4.
20. Walsh, E. E., Hall, C. B., Briscelli, M., Brandriss, M. W., & Schlesinger, J. J. (1997) J. Infect. Dis. 155, 1198-1204.
21. Johnson, P. R. & Collins. P. L. (1988) J. Gen. Virol. 69, 2623-8.
22. Anderson, L. J., Hierholzer, J. C., Tsos, C., Hendry, R. M., Fernie, B. F., Stone, Y. & McIntosh, K. (1985) J. Infect. Dis. 151, 626-633.+
23. Alwan, W. H. & Openshaw, P. J. (1993) Vaccine 11, 431-437.
24. Gaddum, R. M., Cook, R. S., Wyld, S. G., Lopez, J. A., Bustos, R., Melero, J. A. & Taylor, G. (1996) J, Gen. Virol. 77, 1239-1248.
25. Srikjatkhachom, A. & Braciale, T. J. (1997) J. Virol. 71, 678-685.
26. Collins, P. L., Huang, Y. T. & Wertz, G. W. (1984) Proc. Natl. Acad. Sci. USA 81, 7683-7.
27. Sandhu, J. S., Osadjan, M. D., Krasnyanski, S. F., Domier, L. L., Korban, S. S. & Buetow, D. E. (1998) Plant Cell Rep., in press.
28. Deikman, J., Kline, R. & Fischer, R. L. (1992) Plant Physiol. 100, 2013-2017.
29. Konez, C. & Schell, J. (1986) Mol. Gen. Genet. 204, 383-396.
30. Bird, C. R., Smith, C. J., Ray, J. A., Moureau, P., Bevan, M. W., Bird, A. S., Hughes, S., Morris, P. C., Grierson, D. & Schuh, W. (1988) Plant Mol. Biol. 11, 651-66.
31. Hamza, S. & Chupeau, Y. (1993) J. Exp. Bot. 44, 1837-1845.
32. Sambrook, J., Fritsch, E. F. & Maniatis, T. (1989) Molecular Cloning: A Laboratory Manual (Cold Spring Harbor Laboratory Press, Cold Spring Harbor, N.Y.).
33. Clark, M. F. & Adams, A. N. (1977) J. Gen. Virol. 34, 475-483.
34. Bradford, M. M. (1976) Anal. Biochem. 72, 248-254.
35. Mason, H. S., Lam, D. M. & Arntzen, C. J. (1992) Proc. Natl. Acad. Sci. USA 89, 11745-9.
36. Clements, J. D., Lyon, F. L., Lowe, K. L., Farrand, A. L. & el-Morshidy, S. (1986) Infect. Imunun. 53, 685-92.
37. Bentey, P., Ken, L. & Chua, N. H. (1989) EMBO J. 2195-2202.
38. Lincoln, J. E., Cordes, S., Read, E. & Fischer, R. L. (1987) Proc. Natl. Acad. Sci. USA 84, 2793-7.
39. Lincoln, J. E., Cordes. S., Read. E. & Fischer. R. L. (1987) Proc. Natl. Acad Sci USA, 84, 2793-2797.
40. Waris, M. E., Tsou, C., Erdman, D. D., Day, D. B. & Anderson, L. J. (1997) J. Virol. 71, 6935-9.
41. Tristram, D. A., Welliver, R. C., Mohar, C. K., Hogerman, D. A., Hildreth, S. W. & Paradiso, P. (1993) J. Infect. Dis. 167, 191-195.
42. Tristram, D. A., Welliver, R. C., Hogerman, D. A., Hildreth, S. W. & Paradiso, P. (1994) Vaccine 12, 551-556.
43. Belshe, R. B., Anderson, E. L. & Walsh, E. E. (1993) J. Infect. Dis. 168, 1024-1029.
44. Paradiso, P. R., Hildreth. S. W., Hogerman, D. A., Speelman, D. J, Lewin, E. B., Oren. J. & Smith, D. H. (1994) Pediatr. Infect. Dis. J. 13, 792-798.
45. Falsey, A. R. & Walsh, E. E. (1996) Vaccine 14, 1214-8.
46. Piedra, P. A., Grace, S., Jewell, A., Spinelli, S., Bunting, D., Hogerman, D. A., Malinoski, F. & Hiatt. P. W. (1996) Pediatr. Infect. Dis. J. 15, 23-31.
47. Groothais, J. R. King, S. J., Hogerman. D. A., Paradiso, P. R. & Simoes, E. A. F. (1998) J. Infect. Dis. 177, 467-469.
48. Walsh, E. E., Brandrist, M. W. & Schlesinger, J. J. (1985) J. Gen. Virol. 66.408-415.
49. Collins, P. L., McIntosh, K., Chanock, R. M. & Murphy, B. R. (1996) in Fields' Virology. eds. Fields, B. N., Knipe, D. M., Howley, P. M., Chanock, R. M., McInick, J. L., Monath, T. P., Roizman, B. & Straus, S. E. (Lippincott-Raven, Philadelphia, Pa.), Vol. 2, pp. 1313-1351.
50. Jobling, S. A., Gehrke, L. (1987) Nature 325:622-625.
51. Matzke, M. A., EMBO J. 8:643-649.

52. Wallin, A., Johansson, L. (1989) J. Plant Physiol. 135: 565-570.
53. Wilde, R. J., Shufflebottom, D., Cooke, S., Jasinska, I., Merryweather, A., Berl, R., Brammar, W. J., Bevan, M., Schuch, W. (1992) EMBO J. 11:1251-1259.
54. Wang, C. S., Walling, L. L., Eckard, K. J., Lord, E. M. (1992) Am. J. Bot. 79:118-127.
55. Laemmli, U. K. (1970) Nature 227:680-685.
56. Walsh, E. E., Hruska, J. (1983) J. Virol. 47:171-177.
57. Ejdeback, M., Young, S., Samuelson, A., Karlsson, B. G. (1997) Protein Expr. Purif., 11(1):17-25.
58. Andre, S., Eberele, J., Schraut, W., Bultmann, A., Haas, J. (1998) J. Virol., 72(2):1497-503.
59. Impact Study Group, Pediatrics (1998) 102:531-537.
60. Prevent Study Group, Pediatrics (1997) 99:93-99.
61. Am. Acad. Pediatrics Committee on Infectious Diseases, Pediatrics (1996) 97:137-40.
62. Piazza, F. M., Johnson, S. A., Darnell, M. E. R., Porter, D. D., Hemming, V. G., Prince, G. A., Virology (1993) 67(3): 1503-10.
63. Bevan, M., Nucleic Acids Res. (1984) 12: 8711-8721.
64. Mason H, et al., Plant Cell (1993) 5:241-251.
65. An G., Plant Physiol. (1985) 79:568-570.
66. Maniatis, T., Molecular Cloning: A Laboratory Manual (1982) (Cold Spring Harbor Laboratory Press, Cold Spring Harbor, N.Y.).
67. Hood, E. et al., Transgenic Res. (1993) 2: 208-218.
68. Simpson, R. et al., Plant Mol. Biol. (1986) δ: 403-415.
69. Chilton, M-D, Scientific American (1983) 248: 50.
70. Gelvin, S., Plant Physiol. (1990) 92: 281-285.
71. Hooykaas, P. et al., Plant Mol. Biol. (1992) 13: 327-336.
72. Rogers, S. et al. and Horsch, R. et al., Science (1985) 227: 1229-1231.
73. Sukhapinda, K. et al., Plant Mol. Biol. (1987) δ: 209.
74. Evans, D. A. et al., Handbook of Plant Cell Culture (1983) 1, 124.
75. Paszkowski, J. et al., EMBO J. (1984) 3: 2717.
76. Potrykus, I. et al., Mol. Gen. Genet. (1985) 199: 169.
77. Rhodes, C., et al., Bio/Technology (1988) δ: 56.
78. Fromm, M. et al., Nature (1986) 319: 719.
79. Potrykus, I., Bio/Technology (1990) δ: 535-542.
80. Smith, R., et al. Crop Sci. (1995) 35: 301-309].
81. Brisson, N. et al., Nature (1984) 310: 511.
82. Dehayes, A. et al., EMBO J. (1985) 4: 2731.
83. Negrutiu, R. et al., Plant Mol. Biol. (1987) δ: 363.
84. Klein, T. et al., Nature (1987) 327: 70.
85. Sanford, J., Physiol. Plant (1990) 79: 206-209.
86. McCabe, D. et al., Bio/Technology (1988) 6: 923.
87. Whitehead, S. S., Bukreyev, A., Teng, M N, Firestone, C. Y., St. Claire, M., Elkine, W. R., Collins, P. L., Murphy, B. R., J. Virol. (1997) 73(4): 3438-42.
88. Bastien, N., Trudel, M., Simard, C., Vaccine (1999) 17(7-8): 832-6.
89. Herlocher, M. L., Ewasyshyn, M., Sambhara, S., Gharee-Kermani, M., Cho, D., Lai, J., Klein, M., Massab, H. F., Vaccine (1999) 17(2): 172-81.
90. Clark, J. H., Zhou, H. Z., Cheng, X., Coelingh, K., Bryant, M., Li, S., Virology (1998) 251(1):206-14.
91. Power, U. F., Plotnicky-Gilquin, H., Huss, T., Robert, A., Trudel, M., Stahl, S., Uhlen, M., Nguyen, T. N., Binz, H., Virology (1997) 230(2): 155-66.
92. Neuzil, K. M., Johnson, J. E., Tang, Y. W., Prieels, J. P., Slaoui, M., Gar, N., Graham, B. S., Vaccine (1997) 15(5): 525-32.
93. Ellis, J. A., Hassard, L. E., Cortese, V. S., Morley, P. S., J. Am. Vet. Med. Assoc. (1996) 208(3): 393-400.
94. Piedra, P. A., Wyde, P. R., Castleman, W. L., Ambrose, M. W., Jewell, A. M., Speelman, D. J., Hildreth, S. W., Vaccine (1993) 11: 1415-23.
95. Wertz, G. W., et al., Proc. Nat'l. Acad. Sci., USA (1985) 82: 4075-9.
96. Walsh et al., Infect. and Immun., (1984) 43: 756.
97. Prince et al., Virus Res., (1985) 3: 193.
98. Prince et al., J. Virol., (1985) 55: 517.
99. Prince et al., J. Virol., (1987) 61: 1851.
100. Hemming et al., J. Inf Dis., (1985) 52: 1083.
101. Byrd, L. G., Prince, G. A., Clin. Infect. Dis. (1997) 25(6): 1363-8.
102. Kimpen, J. L. L., Reviews in Medical Microbiology (1996) 115-122.
103. Oppenshaw, P. M., Am. J. of Respiratory and Critical Care Medicine (1995) 59-62.
104. Anderson, L. J., Heilman, C. A., J. Infect. Dis. (1995) 171(1): 1-7.
105. Tripp, R. A., Anderson, L. J., J. Virol. (1998) 72(11): 8971-75.
106. Waris, M. E., Tsou, C., Erdman, D. D., Day, D. B., Anderson, L. J., J. Virol. (1997) 71(9): 6935-9).
107. Oppenshaw, P. J., Hussell, T., Dev. Biol. Stand. (1998) 92: 179-85.
108. Hussell, T., Spender, L. C., Georgiou, A., O'Garra, A., Oppenshaw, P. J. Resp. Med. (1996) 77(10): 2447-55.
109. Hancock, G. E., Speelman, D. J., Frenchick, P. J., Mineo-Kuhn, M. M., Baggs, R. B., Halm, D. J., Vaccine (1995) 13(4): 391-400.
110. Chargelegue, D., Obeid, O. E., Hsu, S. C., Shaw, M. D., Denbury, A. N., Taylor, G., Steward, M. W., J. Virol. (1998) 72(3) 2040-6.
111. Hsu, S. C., Chargelegue, D., Steward, M. W., Virol. (1998) 240(2): 376-81.
112. Li, X., Sambhara, S., Li, C. X., Ewasyshyn, M., Parrington, M., Caterini, J., James, O., Cates, G., Du, R. P., Klein, M., J. Exp. Med. (1998) 188(4): 681-8.
113. Walsh, E. E., J. Infect. Dis. (1994) 170(2): 345-50.
114. van Schaik, S. M., Enhorning, G., Vargas, I., Welliver, R. C., J. Infect. Dis., (1998) 177(2): 269-76.
115. Peebles, R. S., Jr., Sheller, J. R., Johnson, J. E., Mitchell, D. B., Graham, B. S., J. Med. Virol. (1999) 57(2): 186-92.
116. Crowe, J. E., Jr., Gilmour, P. S., Murphy, B. R., Chanock, R. M., Duan, L., Pomerantz, R. J., Pilkington, G. R. (1998) 177(4): 1073-6.
117. Graham, B., Kahwash, S., Durbin, J. E. American Meeting of the Society for Pediatric Pathology, Feb. 28-Mar. 1, 1998.
118. Fischer, J. E. et al., J. Virol. (1997) 71(11): 8672-7.
119. Tang, Y. W. et al., Vaccine (1997) 15(6-7): 597-602.
120. Neuzil, K. M. et al., Vaccine (1997) 15(5): 525-32.
121. Graham, B. S. et al., Pediatr. Res. (1993) 34(2): 167-72.
123. Wyde, P. R. et al., Pediatr. Res. (1995) 38(4): 543-50.
124. Piazza, F. M. et al., Pediatr. Pulmolol. (1995) 19(6): 355-9.
125. Sami, I. R. et al., J. Infect. Dis. (1995) 171(2): 440-43.
126. Faverio, L. A. et al., J. Infect. Dis. (1997) 175(4): 932-4.
127. Johnson, S. A. et al., J. Gen. Virol. (1996) 77(1): 101-8.
128. Sullender, W. M. et al., J. Gen. Virol. (1996) 77(4): 641-8.
129. Sullender, W. M., Mechanism of RSV Vaccine Immunopotentiation, National Institute of Allergy and Infectious Diseases Identifying No.: 5R01A137197-04 (1998).
130. Kakuk, T. J. et al., J. Infect. Dis. (1993) 167(3): 553-61.
131. Dakhama, A. et al., Eur. Respir. J. (1997) 10(1): 20-6.
132. Dakhama, A. et al., Pediatric. Pulmonol. (1998) 26(6): 396-404.

133. Hegele, R. G. et al., Eur. Respir. J. (1993) 6(9) 1324-31.
134. Hsu, K. H. et al., Vaccine (1994) 12(7): 607-12.
135. Simoes, E. A., Natural and Vaccine Induced Immunity to RSV in Primates, National Institute of Allergy and Infectious Diseases Identifying No.: 5R01AI37271-04 (1998).
136. Brams, P., Broadly Respiratory Syncytial Virus Neutralizing Human Monoclonal Antibodies, National Institute of Allergy and Infectious Diseases Identifying No.: 5R44AI36027-03 (1998).
137. Bucholz, U. J. et al., J. Virol. (1999) 73(1): 251-259.
138. Collins, P. L et al., J. Virol. (1984) 49:572-8.

What is claimed is:

1. A method for eliciting a Th1 immune response in a subject comprising orally administering to a subject in need thereof an edible portion of a plant comprising a chimeric nucleic acid construct comprising a nucleic acid molecule encoding an antigenic respiratory syncytial virus (RSV)-F protein or antigenic peptide of the RSV-F protein in an amount that induces RSV-F-specific serum IgG and IgA and RSV-F-specific mucosal IgA, wherein said antigenic RSV-F protein or antigenic peptide of the RSV-F protein is expressed in the edible portion of the plant and elicits a Th1 immune response in the subject.

2. The method of claim 1, wherein said administration comprises a prime vaccination.

3. The method of claim 1, wherein said administration further comprises a boost vaccination.

* * * * *